(12) United States Patent
Chen et al.

(10) Patent No.: US 10,208,003 B2
(45) Date of Patent: *Feb. 19, 2019

(54) SYNTHESIS OF AMINE SUBSTITUTED 4,5,6,7-TETRAHYDROBENZOTHIAZOLE COMPOUNDS

(71) Applicant: KNOPP BIOSCIENCES LLC, Pittsburgh, PA (US)

(72) Inventors: Weirong Chen, Waltham, MA (US); Michael Humora, Cranbury, NJ (US); Daw-Iong Albert Kwok, Gillette, NJ (US); William F. Kiesman, Wayland, MA (US); Erwin Ayandra Irdam, Melrose, MA (US)

(73) Assignee: Knopp Biosciences LLC, Pittsburgh, PA (US)

( * ) Notice: Subject to any disclaimer, the term of this patent is extended or adjusted under 35 U.S.C. 154(b) by 125 days.

This patent is subject to a terminal disclaimer.

(21) Appl. No.: 15/332,599

(22) Filed: Oct. 24, 2016

(65) Prior Publication Data

US 2017/0158648 A1   Jun. 8, 2017

Related U.S. Application Data

(63) Continuation of application No. 14/366,590, filed as application No. PCT/US2012/071335 on Dec. 21, 2012, now Pat. No. 9,512,096.

(60) Provisional application No. 61/579,188, filed on Dec. 22, 2011.

(51) Int. Cl.
*C07D 277/82* (2006.01)
*C07D 277/62* (2006.01)

(52) U.S. Cl.
CPC ......... *C07D 277/82* (2013.01); *C07D 277/62* (2013.01)

(58) Field of Classification Search
None
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 4,031,894 A | 6/1977 | Urquhart et al. |
| 4,144,317 A | 3/1979 | Higuchi et al. |
| 4,201,211 A | 5/1980 | Chandrasekaran et al. |
| 4,286,592 A | 9/1981 | Chandrasekaran et al. |
| 4,314,557 A | 2/1982 | Chandrasekaran et al. |
| 4,327,725 A | 5/1982 | Cortese et al. |
| 4,379,454 A | 4/1983 | Campbell et al. |
| 4,395,859 A | 8/1983 | Rohrer |
| 4,435,180 A | 3/1984 | Leeper |
| 4,559,222 A | 12/1985 | Enscore et al. |
| 4,568,343 A | 2/1986 | Leeper et al. |
| 4,573,995 A | 3/1986 | Chen et al. |
| 4,588,580 A | 5/1986 | Gale et al. |
| 4,612,008 A | 9/1986 | Wong et al. |
| 4,626,539 A | 12/1986 | Aungst et al. |
| 4,645,502 A | 2/1987 | Gale et al. |
| 4,698,062 A | 10/1987 | Gale et al. |
| 4,704,282 A | 11/1987 | Campbell et al. |
| 4,725,272 A | 2/1988 | Gale |
| 4,731,374 A | 3/1988 | Griss et al. |
| 4,781,924 A | 11/1988 | Lee et al. |
| 4,783,337 A | 11/1988 | Wong et al. |
| 4,788,062 A | 11/1988 | Gale et al. |
| 4,806,341 A | 2/1989 | Chien et al. |
| 4,816,258 A | 3/1989 | Nedberge et al. |
| 4,843,086 A | 6/1989 | Griss et al. |
| 4,849,226 A | 7/1989 | Gale |
| 4,886,812 A | 12/1989 | Griss et al. |
| 4,904,475 A | 2/1990 | Gale et al. |
| 4,908,027 A | 3/1990 | Enscore et al. |
| 4,917,895 A | 4/1990 | Lee et al. |
| 4,938,759 A | 7/1990 | Enscore et al. |
| 4,943,435 A | 7/1990 | Baker et al. |
| 5,004,610 A | 4/1991 | Osborne et al. |
| 5,024,843 A | 6/1991 | Kuczynski et al. |
| 5,069,909 A | 12/1991 | Sharma et al. |
| 5,071,656 A | 12/1991 | Lee et al. |
| 5,082,668 A | 1/1992 | Wong et al. |
| 5,091,190 A | 2/1992 | Kuczynski et al. |
| 5,112,842 A | 5/1992 | Zierenberg et al. |
| 5,122,382 A | 6/1992 | Gale et al. |
| 5,141,750 A | 8/1992 | Lee et al. |
| 5,284,660 A | 2/1994 | Lee et al. |
| 5,314,694 A | 5/1994 | Gale et al. |
| 5,342,623 A | 8/1994 | Enscore et al. |
| 5,411,740 A | 5/1995 | Lee et al. |
| 5,442,117 A | 8/1995 | Stahley et al. |
| 5,545,413 A | 8/1996 | Kuczynski et al. |
| 5,591,454 A | 1/1997 | Kuczynski et al. |

(Continued)

FOREIGN PATENT DOCUMENTS

| | | |
|---|---|---|
| AU | 2006279643 B2 | 8/2006 |
| AU | 2002360600 B2 | 3/2008 |

(Continued)

OTHER PUBLICATIONS

Hardy et al. "Genetic Classification of Primary Neurodegenerative Disease" Nov. 6, 1998 Science 282(5391):1075-1079.

(Continued)

*Primary Examiner* — Nyeemah A Grazier
(74) *Attorney, Agent, or Firm* — Pepper Hamilton LLP

(57) ABSTRACT

The present invention is related to an improved process for the preparation of amino-substituted 4,5,6,7-tetrahydrobenzothiazole compounds of formula I, such as the compound 2-amino-4,5,6,7-tetrahydro-6-(n-propylamino)benzothiazole. The invention further relates to an improved synthesis of (R)-2-amino-4,5,6,7-tetrahydro-6-(n-propylamino)benzothiazole. The invention also relates to the methods and intermediates associated with the synthetic process.

65 Claims, 3 Drawing Sheets

(56) References Cited

U.S. PATENT DOCUMENTS

| | | |
|---|---|---|
| 5,635,203 A | 6/1997 | Gale et al. |
| 5,650,420 A | 7/1997 | Hall et al. |
| 5,674,895 A | 10/1997 | Guittard et al. |
| 5,719,060 A | 2/1998 | Hutchens et al. |
| 5,792,664 A | 8/1998 | Chait et al. |
| 5,804,215 A | 9/1998 | Cubbage et al. |
| 5,830,497 A | 11/1998 | Yamanaka et al. |
| 5,840,754 A | 11/1998 | Guittard et al. |
| 5,912,268 A | 6/1999 | Guittard et al. |
| 6,043,251 A | 3/2000 | Douillet et al. |
| 6,156,777 A | 12/2000 | Hall et al. |
| 6,187,802 B1 | 2/2001 | Cheetham et al. |
| 6,197,339 B1 | 3/2001 | Ju |
| 6,228,398 B1 | 5/2001 | Devane et al. |
| 6,255,329 B1 | 7/2001 | Maj |
| 6,262,115 B1 | 7/2001 | Guittard et al. |
| 6,284,774 B1 | 9/2001 | Wright et al. |
| 6,294,790 B1 | 9/2001 | Weinberger |
| 6,443,976 B1 | 9/2002 | Flower et al. |
| 6,458,820 B1 | 10/2002 | Hall et al. |
| 6,480,820 B1 | 11/2002 | Clopton et al. |
| 6,541,486 B1 | 4/2003 | Bitler et al. |
| 6,618,138 B2 | 9/2003 | Khoury |
| 6,667,329 B1 | 12/2003 | Maj |
| 6,675,104 B2 | 1/2004 | Paulse et al. |
| 6,727,367 B2 | 4/2004 | Pospisilik |
| 6,730,325 B2 | 5/2004 | Devane et al. |
| 6,750,235 B1 | 6/2004 | Rosenbaum |
| 6,776,984 B1 | 8/2004 | Schwartz |
| 6,793,936 B2 | 9/2004 | Devane et al. |
| 6,902,742 B2 | 6/2005 | Devane et al. |
| 6,919,092 B2 | 7/2005 | Guittard et al. |
| 6,919,373 B1 | 7/2005 | Lam et al. |
| 6,927,036 B2 | 8/2005 | Gallop et al. |
| 6,929,801 B2 | 8/2005 | Klose et al. |
| 6,930,129 B2 | 8/2005 | Lam et al. |
| 7,005,255 B2 | 2/2006 | Kaddurah-Daouk et al. |
| 7,157,480 B2 | 1/2007 | Bennett, Jr. |
| 7,344,733 B2 | 3/2008 | Beier et al. |
| 7,572,596 B2 | 8/2009 | Bowser |
| 7,741,490 B2 | 6/2010 | Castaldi et al. |
| 8,017,598 B2 | 9/2011 | Bozik et al. |
| 8,186,890 B2 | 5/2012 | Lu |
| 8,192,091 B2 | 6/2012 | Hsu et al. |
| 8,408,815 B2 | 4/2013 | Lin et al. |
| 2002/0004058 A1 | 1/2002 | Yoshii et al. |
| 2002/0103240 A1 | 8/2002 | Pospisilik |
| 2002/0106731 A1 | 8/2002 | Ruben et al. |
| 2002/0151526 A1 | 10/2002 | Gallop et al. |
| 2002/0177626 A1 | 11/2002 | Cook et al. |
| 2003/0013120 A1 | 1/2003 | Patz et al. |
| 2003/0049318 A1 | 3/2003 | Davis et al. |
| 2003/0166696 A1 | 9/2003 | Warsinksy et al. |
| 2003/0203055 A1 | 10/2003 | Rao et al. |
| 2004/0014721 A1 | 1/2004 | Hensley et al. |
| 2004/0031667 A1 | 2/2004 | Dinkel et al. |
| 2004/0033530 A1 | 2/2004 | Awrey et al. |
| 2004/0067991 A1 | 4/2004 | Greig et al. |
| 2004/0097540 A1 | 5/2004 | Peters et al. |
| 2004/0122104 A1 | 6/2004 | Hirsh et al. |
| 2004/0132788 A1 | 7/2004 | Chabrier De Lassauniere et al. |
| 2004/0132826 A1 | 7/2004 | Hirsh et al. |
| 2004/0219213 A1 | 11/2004 | Burnside et al. |
| 2004/0247656 A1 | 12/2004 | Beier et al. |
| 2004/0265370 A1 | 12/2004 | Odidi et al. |
| 2005/0031667 A1 | 2/2005 | Patel et al. |
| 2005/0032856 A1 | 2/2005 | Bennett, Jr. et al. |
| 2005/0053649 A1 | 3/2005 | Chalmers |
| 2005/0059717 A1 | 3/2005 | Van Eupen et al. |
| 2005/0070715 A1 | 3/2005 | Bhat et al. |
| 2005/0074865 A1 | 4/2005 | Afeyan et al. |
| 2005/0089575 A1 | 4/2005 | Friedl et al. |
| 2005/0148026 A1 | 7/2005 | Bowser et al. |
| 2005/0208156 A1 | 9/2005 | Ploch et al. |
| 2005/0220877 A1 | 10/2005 | Patel et al. |
| 2005/0226926 A1 | 10/2005 | Amidon et al. |
| 2005/0265379 A1 | 12/2005 | Rao |
| 2006/0009659 A1 | 1/2006 | Keil et al. |
| 2006/0046967 A1 | 3/2006 | Satyam |
| 2006/0051419 A1 | 3/2006 | Friedl et al. |
| 2006/0069263 A1 | 3/2006 | Gribun et al. |
| 2006/0099257 A1 | 5/2006 | Langridge et al. |
| 2006/0106224 A1 | 5/2006 | Gupta et al. |
| 2006/0110450 A1 | 5/2006 | Eisenreich |
| 2006/0121619 A1 | 6/2006 | Bowser |
| 2006/0128643 A1 | 6/2006 | Kaddurah-Daouk et al. |
| 2006/0141037 A1 | 6/2006 | Mehta et al. |
| 2006/0148866 A1 | 7/2006 | Xia et al. |
| 2006/0281797 A1 | 12/2006 | Bennett, Jr. |
| 2006/0286167 A1 | 12/2006 | Staunton et al. |
| 2007/0087410 A1 | 4/2007 | Lanahan et al. |
| 2007/0105918 A1 | 5/2007 | Bennett, Jr. |
| 2007/0203209 A1 | 8/2007 | Bartolini et al. |
| 2007/0259930 A1 | 11/2007 | Bozik et al. |
| 2008/0014259 A1 | 1/2008 | Bozik et al. |
| 2008/0020028 A1 | 1/2008 | Shevchuk et al. |
| 2008/0026043 A1 | 1/2008 | Mueller et al. |
| 2008/0081041 A1 | 4/2008 | Nemeth |
| 2008/0096939 A1 | 4/2008 | Keil et al. |
| 2008/0194832 A1 | 8/2008 | Silva Guisasola et al. |
| 2008/0227985 A1 | 9/2008 | Raje et al. |
| 2008/0234338 A1 | 9/2008 | Bennett, Jr. |
| 2009/0042956 A1 | 2/2009 | Bozik et al. |
| 2009/0054504 A1 | 2/2009 | Bozik et al. |
| 2009/0105483 A1 | 4/2009 | Balicki et al. |
| 2009/0149518 A1 | 6/2009 | Nishii et al. |
| 2010/0291073 A1 | 11/2010 | Koiki et al. |
| 2010/0292149 A1 | 11/2010 | Bowser |
| 2011/0009460 A1 | 1/2011 | Gribkoff et al. |
| 2011/0020339 A1 | 1/2011 | Hargreave et al. |
| 2011/0190356 A1 | 8/2011 | Bozik et al. |
| 2011/0218222 A1 | 9/2011 | Bennett, Jr. |
| 2011/0224268 A1 | 9/2011 | Bozik et al. |
| 2011/0293718 A1 | 12/2011 | Bozik et al. |
| 2011/0301210 A1 | 12/2011 | Bennett, Jr. |
| 2012/0134929 A1 | 5/2012 | McGrath et al. |
| 2012/0142715 A1 | 6/2012 | Kim |
| 2012/0148575 A1 | 6/2012 | Koike et al. |
| 2012/0225915 A1 | 9/2012 | Bozik et al. |
| 2012/0253047 A1 | 10/2012 | Allegrini et al. |
| 2012/0258994 A1 | 10/2012 | McKinney et al. |
| 2013/0059801 A1 | 3/2013 | Milne et al. |
| 2013/0079526 A1 | 3/2013 | Greenfield et al. |
| 2013/0116292 A1 | 5/2013 | Bennett, Jr. |
| 2013/0123312 A1 | 5/2013 | Bozik et al. |
| 2013/0172394 A1 | 7/2013 | Bennett, Jr. |
| 2013/0230569 A1 | 9/2013 | Bozik et al. |
| 2013/0245081 A1 | 9/2013 | Gribkoff et al. |
| 2013/0273557 A1 | 10/2013 | Gribkoff et al. |
| 2013/0310430 A1 | 11/2013 | Bozik et al. |
| 2014/0018343 A1 | 1/2014 | Romero et al. |
| 2014/0031401 A1 | 1/2014 | Bozik et al. |
| 2014/0100372 A1 | 4/2014 | Raje et al. |
| 2014/0329869 A1 | 11/2014 | Bozik et al. |
| 2015/0018397 A1 | 1/2015 | Bozik et al. |
| 2015/0126745 A1 | 5/2015 | Chen et al. |
| 2016/0022647 A1 | 1/2016 | Bozik et al. |
| 2016/0030397 A1 | 2/2016 | Bozik et al. |
| 2016/0158205 A1 | 6/2016 | Bozik et al. |
| 2016/0193186 A1 | 7/2016 | Bozik et al. |
| 2016/0193187 A1 | 7/2016 | Bozik et al. |

FOREIGN PATENT DOCUMENTS

| | | |
|---|---|---|
| AU | 2007333050 B2 | 12/2013 |
| CA | 2619217 A1 | 2/2007 |
| CA | 2605078 A1 | 1/2013 |
| CN | 1308533 A | 8/2001 |
| CN | 1617720 A | 5/2005 |
| CN | 1735604 A | 2/2006 |
| CN | 101677564 A | 3/2010 |
| CN | 102160865 A | 8/2011 |
| CN | 102772404 A | 11/2012 |
| EP | 0186087 A1 | 7/1986 |

(56) References Cited

FOREIGN PATENT DOCUMENTS

| | | |
|---|---|---|
| EP | 0558861 A1 | 9/1993 |
| EP | 2156833 A1 | 2/2010 |
| EP | 1453505 B1 | 9/2010 |
| EP | 2305252 A1 | 4/2011 |
| EP | 2442655 | 4/2012 |
| EP | 2465500 A | 6/2012 |
| EP | 2497472 A1 | 9/2012 |
| EP | 2497473 A1 | 9/2012 |
| EP | 2497474 A1 | 9/2012 |
| EP | 2542541 A | 1/2013 |
| EP | 2246053 B1 | 9/2013 |
| JP | 61-155377 | 7/1986 |
| JP | H07504655 A | 5/1995 |
| JP | 10-510809 A | 10/1998 |
| JP | 2006-143708 | 6/2006 |
| JP | 2009-504748 A | 2/2009 |
| JP | 2010-031059 A | 2/2010 |
| JP | 2010-513316 A | 4/2010 |
| JP | 4500543 | 4/2010 |
| JP | 11-515012 A | 5/2011 |
| RU | 2009 126742 A | 1/2011 |
| WO | WO 1993/17683 A1 | 9/1993 |
| WO | WO 1993/24834 A1 | 12/1993 |
| WO | WO 1996/18395 A | 6/1996 |
| WO | WO 1997/15304 A1 | 5/1997 |
| WO | WO 1998/59360 A1 | 12/1998 |
| WO | WO 2001/13902 A2 | 3/2001 |
| WO | WO 2001/22820 A1 | 4/2001 |
| WO | WO 2001/62249 A1 | 8/2001 |
| WO | WO 2003/049705 A2 | 6/2003 |
| WO | WO 03/070188 A2 | 8/2003 |
| WO | WO 2004/002520 A1 | 1/2004 |
| WO | WO 2004/010999 A1 | 2/2004 |
| WO | WO 2004/026246 A2 | 4/2004 |
| WO | WO 2004/041797 A1 | 5/2004 |
| WO | WO 2004/050034 A2 | 6/2004 |
| WO | WO 2004/058163 A2 | 7/2004 |
| WO | WO 2005/011687 A1 | 2/2005 |
| WO | WO 2005/092871 A2 | 10/2005 |
| WO | WO 2005/123193 A2 | 12/2005 |
| WO | WO 2006/003471 A1 | 1/2006 |
| WO | WO 2006/012277 A | 2/2006 |
| WO | WO 2006/015943 A2 | 2/2006 |
| WO | WO 2006/015944 A2 | 2/2006 |
| WO | WO 2006/43532 A1 | 4/2006 |
| WO | WO 2006/076681 A2 | 7/2006 |
| WO | WO 2006/116369 A2 | 11/2006 |
| WO | WO 2007/022182 A1 | 2/2007 |
| WO | WO 2007/045620 A | 4/2007 |
| WO | WO 2007/075095 A1 | 7/2007 |
| WO | WO 2007/076062 A2 | 7/2007 |
| WO | WO 2007/090882 A2 | 8/2007 |
| WO | WO 2007/121188 A | 10/2007 |
| WO | WO 2007/137071 A2 | 11/2007 |
| WO | WO 2008/023027 A2 | 2/2008 |
| WO | WO 2008/041240 A1 | 4/2008 |
| WO | WO 2008/52953 A1 | 5/2008 |
| WO | WO 2008/074033 A1 | 6/2008 |
| WO | WO 2008/104847 A2 | 9/2008 |
| WO | WO 2008/113003 A1 | 9/2008 |
| WO | WO 2008/113056 A2 | 9/2008 |
| WO | WO 2010/022140 A1 | 2/2010 |
| WO | WO 2010/148409 A1 | 12/2010 |
| WO | WO 2011/109596 A1 | 9/2011 |
| WO | WO 2011/150221 A2 | 12/2011 |
| WO | WO 2012/019015 A2 | 2/2012 |
| WO | 2013034550 A1 | 3/2013 |
| WO | WO 2013/096816 A1 | 6/2013 |
| WO | WO 2013/096870 A1 | 6/2013 |
| WO | WO 2014/134569 A1 | 9/2014 |
| WO | WO 2015/006708 A1 | 1/2015 |
| WO | WO 2015/0018397 A1 | 1/2015 |
| WO | WO 2015/023786 A1 | 2/2015 |
| WO | WO 2015/023790 A1 | 2/2015 |

OTHER PUBLICATIONS

Hasegawa et al. "A New Process for Synthesis of the Astrcyte Activation Suppressor ONO-2506" 2005 Organic Proc. Res. & Dev. 9:774-781.

Khan et al. "Alzheimer's disease cybrids replicate beta-amyloid abnormalities through cell death pathways" Aug. 2000 Ann Neurol. 48(2):148-55. PubMed PMID: 10939564.

Kieburtz "Safety and Efficacy of Pramipexole in Early Parkinson Disease" 1997 JAMA 278(2):125-130.

Lucchinetti et al. "Inflammatory Cortical Demyelination in Early Multiple Sclerosis" The New England Journal of Medicine (2011) (365) pp. 2188-2197.

Roca-Santiago et al. "Alzheimer's Disease and Age-related Macular Degeneration" Feb. 2006 Arch. Soc. Esp. Oftalmol. 81(2):73-78.

Rothstein et al. "β-Lactam antibiotics offer neuroprotection by increasing glutamate transporter expression" Jan. 6, 2005 Nature 433(7021):73-77.

Liou et al. ("Case Report Churg-Strauss syndrome presented as multiple intracerebral hemorrhage." Lupus (1997);6:279-282).

Uemichi et al. "A New Mutant Transthyretin (Arg 10) Associated with Familial Amyloid Polyneuropathy" 1992 J. Med. Genet. 29:888-891.

Weller et al. "The idiopathic hypereosinophilic syndrome." Blood 83.10 (1994): 2759-2779.

Abrahamson et al. "Structure and expression of the human cystatin C gene" 1990, Biochem J. 268(2):287-294.

Abramova et al. "Inhibition by R(+) or S(−) Pramipexole of Caspase Activation and Cell Death Induced by Methylpyridinium Ion or Beta Amyloid Peptide in SH-SY5Y Neuroblastoma" 2002, J. Neuroscience Res. 67(4):494-500.

Agardh et al. "Expression of antioxidant enzymes in rat retinal ischemia followed by reperfusion" Jul. 2006, Metabolism 55(7):892-898 (Abstract).

Aguila et al. "Prognosis in Amyotrophic Lateral Sclerosis: A population based study" 2003, Neurology 60:813-819.

Akintola-Ogunremi et al., "Chronic lymphocytic leukemia presenting with symptomatic centeral nervous system involvement," Ann. Hematol. (2002), (81) pp. 402-404.

Anonymous "Variant of Parkinson's Drug Tested in ALS" Jul. 19, 2006 (printed from www.als-mda.org/research/news/060719als_pramipexole.html on Feb. 21, 2008) (Abstract).

Anosova et al. "Antigenecity and Immunogenicity of Allogeneic Retinal Transplants" Oct. 2001, J. Clin. Invest. 108(8):1175-1183.

Ansel et al. "Pharmaceutical Dosage Forms and Drug Delivery Systems, 6th ed." 1995, Williams and Wilkins Media, Malvern, PA (TOC).

Anthony et al. (Nat Rev Immunol Dec. 2007; 7(12):975-987.

Arico et al., Restless Legs Syndrome as the Presenting Symptom of Multiple Myeloma, Journal of Clinical Sleep Medicine (2013), 9(4) pp. 383-385.

Asgeirsson et al. "Hereditary cystatin C amyloid angiopathy: monitoring the presence of the Leu-684→Gln cystatin C variant in cerebrospinal fluids and monocyte cultures by MS" 1998, Biochem. J, 329 (Pt 3):497-503 (1998).

Ashcroft et al. "An Efficient and Scalable Synthesis of the Endothelin Antagonists UK-350,926 and UK-349,862 Using a Dynamic Resolution Process" 2005, Organic Proc. Res. & Dev. 9:663-669.

Balicki et al. "A New, Efficient and Economic Method for Preparation of Pramipexole" May 16, 2006, Book of Abstracts: The Fifth Multidisciplinary conference on Drug Research, Pielaszek Research (Warszawa, Poland) Poster No. 1-19, p. 30 (English Abstract).

Balicki et al. "New method for preparing pramipexole dihydrochloride monohydrate" 2006, Przemysl Chemiczny 85(5):344-346.

Banker et al. "Modern Pharmaceutics" 1979, Marcel Dekker, Inc. (TOC).

Beal "Oxidative Metabolism" 2000, Ann. N.Y. Acad. Sci. 924:164-169.

Beatty et al. "The Role of Oxidative Stress in the Pathogenesis of Age-Related Macular Degeneration" 2000, Surv. Opthalmol 45(2):115-134.

(56) References Cited

OTHER PUBLICATIONS

Benson et al. "Identification of carriers of a variant plasma prealbumin (transthyretin) associated with familial amyloidotic polyneuropathy type J" 1985, J. Clin. Invest. 74:71-75.
Berge et al. "Pharmaceutical Salts" 1977, J. Pharm. Sciences 66(1):1-19.
Bergen et al. "Identification of transthyretin variants by sequential proteomic and genomic analysis" 2004, Clin. Chem. 50(9):1544-1552.
Bernstein et al. "Transythyretin: Its response to malnutrition and stress injury. Clinical usefulness and economic implications" Dec. 2002, Clin. Chem. Lab. Med. 40(12):1344-1348.
Biglan et al. "A Review of Pramipexole and its Clinical Utility in Parkinson's Disease" 2002, Expert Opinion Pharmacotherapy 3(2):197-210.
Borchelt et al. "Superoxide dismutase 1 with mutations linked to familial amyotrophic lateral sclerosis possesses significant activity" 1994, PNAS USA 91(17):8292-8296.
Bozik et al. "Safety, Tolerability, and Pharmacokinetics of KNS-760704 (Dexpramipexole) in Healthy Adult Subjects" 2011, J. Clin. Pharmacol. 51:1177-1185.
Carvey, et al. "Attenuation of levodopa-induced toxicity in mesencephalic cultures by pramipexole" 1997, J. Neural. Transm. 209-228.
Cassarino et al. "An evaluation of the role of mitochondria in neurodegenerative diseases: mitochondrial mutations and oxidative pathology, protective nuclear responses, and cell death in neurodegeneration" 1999, Brain Res. Rev. 29:1-25.
Cassarino et al. "Cyclosporin A increases resting mitochondrial membrane potential in SY5Y cells and reverses the depressed mitochondrial membrane potential of Alzheimer's disease cybrids" May 13, 1998, Biochem. and Biophysical Research Comm. 248:168-173.
Cassarino et al. "Interaction among mitochondria, mitogen-activated protein kinases, and nuclear factor-kappaB in cellular models of Parkinson's disease" Apr. 2000, J Neurochem. 74(4):1384-92. PubMed PMID: 10737593.
Cassarino et al. "Pramipexole reduces reactive oxygen species production in vivo and in vitro and inhibits the mitochondrial permeability transition produced by the parkinsonian neurotoxin methylpyridinium ion" 1998, J. Neurochem. 71(1):295-301.
Cleveland et al. "From Charcot to Lou Gehrig: deciphering selective motor neuron death in ALS" Nov. 2001, Nature 2:806-819.
Corcoran et al. "Absence of retinoids can induce motoneuron disease in the adult rat and a retinoid defect is present in motoneuron disease patients" 2002, J. Cell. Sci. 115:4735-4741.
Corrigan et al. "Comparison of Pramipexole, Fluoxetine, and Placebo in Patients with Major Depression" 2000, Depression and Anxiety 11:58-65.
Cudkowicz et al. "Measures and Markers in Amyotrophic Lateral Sclerosis" Apr. 2004, NeuroRx: The Journal of the American Society for Experimental NeuroTherapeutics 1(2):273-283.
Cudkowicz et al. "Dexpramipexole versus placebo for patients with amyotrophic lateral sclerosis (EMPOWER): a ramdomised double-blind, phase 3 trial" Lancet Neurol. (2013), (12) pp. 1059-1067.
Danzeisen et al. "Targeted Antioxidative and Neuroprotective Properties of the Dopamine Agonist Pramipexole and Its Nondopaminergic Enantiomer SND919CL2x [(+)2-Amino-4, 5, 6, 7-tetrahydro-6-L-propylamino-benzathiazole Dihydrochloride]" 2006, J. Pharmacol. Exp. Ther. 316:189-199.
Davis et al. (Cancer Immunol Res. 2014;2:1-8—p. 5, Fig. 2).
Declaration of James P. Bennett Under 37 C.F.R. 1.132 dated Dec. 15, 2009.
Deigner et al. "Apoptosis Modulators in the Therapy of Neurodegenerative Diseases" Apr. 2000, Ex. Opin. Investigational Drugs 9(4):747-764 XP001012423.
Deng et al. "Elevation of cystatin C in susceptible neurons in Alzheimer's disease" Sep. 2001, Am. J. Pathol. 159(3):1061-1068.

Dooley et al. "Pramipexole. A Review of its Use in the Managemetn of Early and Advanced Parkinson's Disease" Jun. 1998, Drugs Aging 12(6):495-514.
Drobny et al. "Possible Extrapyramidal System Degradation in Parkinson's Disease" 2000, Brain Research Bulletin 53(4):425-430.
Email correspondence from James P. Bennett to Michael Bozik dated May 11, 2006 with a presentation entitled "ALS: An Investigator's View of the Disease and its Treatment".
Email correspondence from James P. Bennett to Michael Bozik dated Oct. 9, 2006 with a draft grant application.
Email correspondence from James P. Bennett to Michael Bozik dated Apr. 6, 2007 with a draft manuscript entitled "R(+) Pramipexole as a Neuroprotectant I: Effects of R(+) Pramipexole Treatment of ALS on ALSFRSr, Forced Vital Capacity and Neurophysiological Index".
Email correspondence from James P. Bennett to Michael Bozik dated Apr. 6, 2007 with a draft manuscript entitled "R(+) Pramipexole as a Neuroprotectant II: Tolerability and Pharmacokinetics in ALS of Esclating Doses to 300mg/day".
European Seach Report and Opinion dated Aug. 1, 2012 for EP 12163888.
European Search Report and Opinion dated Aug. 2, 2012 for EP 12164060.
European Search Report and Opinion dated May 10, 2012 for EP 11186875.
European Search Report dated Feb. 18, 2011 for EP10009931.
European Supplemental Search Report dated Apr. 8, 2010 for EP 08743922.
European Supplemental Search Report dated Apr. 9, 2010 for EP 08732306.9.
European Supplemental Search Report dated Nov. 23, 2006 for EP 02795869.
European Supplemental Search Report dated Oct. 4, 2010 for EP 10008579.4.
Extended European Search Report and Written Opinion dated Sep. 11, 2012 for EP 12164067.
Extended European Supplemental Search Report and Written Opinion dated Feb. 18, 2011 for EP10075571.
Feher et al. "Mitochondrial alternations of retinal pigment epithelium in age-related macular degenteration" Jun. 2006 (Printed from http://www.neurobiologyofaging.org/article/PIISO1974580005001545 on Dec. 11, 2009) Neurobiology of Aging 27(7) (Abstract, 2 pages).
Ferger et al. "The dopamine agonist pramipexole scavenges hydroxyl free radicals induced by striatal application of 6-hydroxydopamine in rats: an in vivo microdialysis study" Aug. 29, 2000, Brain Research 883:216-223.
Gennaro "Remington: The Science and Practice of Pharmacy, 20$^{th}$ Ed." Lippincott Williams & Wlkins, Baltimore, MD, 2000, Ch. 38:704-720.
Golebiewski et al. "Application of GC/MS for Identyfication of the Sideproducts in a Process of Preparation of Pramipexole" May 16, 2006, Book of Abstracts: The Fifth Multidisciplinary conference on Drug Research, Pielaszek Research (Warszawa, Poland) Poster No. 1-57, p. 49.
Goodall et al. "Association of the H63D polymorphism in the hemochromatosis gene with sporadic ALS" 2005, Neurology 65(6):934-937.
Goodman et al. "The Pharmaceutical Basis of Therapeutics, 6$^{th}$ Ed." 1980, MacMillan Publishing Co., New York (TOC).
Gu et al. "Pramipexole protects against apoptotic cell death by non-dopaminergic mechanisms" 2004, J. Neurochem. 91:1075-1081.
Gurney et al. "Benefit of Vitamin E, Riluzole, and Gabapentin in a Transgenic Model of Familial Amyotrophic Lateral Sclerosis" Feb. 1996, Ann. Neurol. 39(2):147-157.
Gurney et al. "Motor Neuron Degeneration in Mice That Express a Human Cu, Zn Superoxide Dismutase Mutation" Jun. 17, 1994, Science 264:1772-1775.
Haghikia et al. "Therapies for multiple sclerosis: translation achievements and outstanding needs" May 2013 Trends in Moleecular Medicine 19(5):309-319.

(56) References Cited

OTHER PUBLICATIONS

Halestrap "The Role of Mitochondria in Cell Death" Mar. 24, 2003, Endocrine Abstracts 5:513 (Abstract).
Hall et al. "Brain hydroxyl radical generation in acute experimental head injury" Feb. 1993, J. Neurochem. 60(2):588-594.
Hall et al. "Neuroprotective effects of the dopamine $D_2 / D_3$ agonist pramipexole against postischemic or methamphetamine-induced degeneration of nigrostriatal neurons" Aug. 6, 1996, Brain Research 742:80-88 (abstract).
Hansen et al. "First Generation Process for the Preparation of the DPP-IV Inhibitor Sitagliptin" 2005, Organic Proc. Res. & Dev. 9:634-639.
Hubble Pre-clinical Studies of Pramipexole: Clinical Relevance May 2000 Eur. J. Neurol. 7(Supp 1):15-20.
Initial Scientific Discussion for the Approval of Mirapex from the European Agency for the Evaluation of Medicinal Products (EMEA), 2005, www.emea.europa.eu/humandocs/PDFS/EPAR/Mirapexin/059097en6.pdf.
International Search Report and Written Opinion for PCT/US2008/057158 dated Jun. 29, 2009.
International Search Report and Written Opinion for PCT/US2010/39379 dated Aug. 25, 2010.
International Search Report and Written Opinion for PCT/US2013/054804 dated Mar. 21, 2014.
International Search Report and Written Opinion for PCT/US2014/019668 dated Jun. 9, 2014.
International Search Report and Written Opinion for PCT/US2014/050951.
International Search Report and Written Opinion for PCT/US2014/050943.
International Search Report for PCT/US2002/39970 dated Jul. 17, 2003.
International Search Report for PCT/US2006/031831 dated Dec. 12, 2006.
International Search Report for PCT/US2007/087639 dated Apr. 4, 2008.
International Search Report for PCT/US2008/057059 dated Jul. 11, 2008.
International Search Report for PCT/US2009/54292 dated Oct. 22, 2009.
International Search Report for PCT/US2011/38159 dated Dec. 12, 2011.
International Search Report for PCT/US2014/046380 dated Dec. 10, 2014.
Jacques et al. "Enantiomers, Racemates and Resolutions" 1981, John Wley and Sons, Inc., New York (TOC).
Johnson et al. (Relationships between drug activity and NCI preclinical in vitro and in vivo models and early clinical trials; British Journal of Cancer; (2001) 84 (10), 1424-1431).
Kamel et al. "Lead exposure and amyotrophic lateral sclerosis" May 2002, Epidemiology 13(3):311-319.
Kato et al. "A neurosphere-derived factor, cystatin C, supports differentiation of ES cells into neural stem cells" Apr. 11, 2006, PNAS USA 103(15):6019-6024.
Kitamura et al. "Protective Effects of the Antiparkinsonian Drugs Talipexole and Pramipexole against 1-Methyl-4-phenylpyridinium-Induced Apoptotic Death in Human Neuroblastoma SH-SY5Y Cells" 1998, Molecular Pharmacology 54:1046-1054.
Lahortiga et al. "Activity of imatinib in systemic mastocytosis with chronic basophilic leukemia and a PRKG2-PDGFRB fusion" 2008, Haematological/The Hematology Journal 93(1): 51-52, 55.
Le et al. "Antioxidant property of pramipexole independent of dopamine receptor activation in neuroprotection" 2000, J. Neural. Transm. 107(10):1165-73.
Lee et al. "Carcinogenicity Predictions for a Group of 30 Chemicals Undergoing Rodent Cancer Bioassays Based on Rules Derived from Subchronic Organ Toxicities" Oct. 1996, Environmental Health Perspectives 104(5):1059-1063.

Levy et al. "Stroke in Icelandic Patients With Hereditary Amyloid Angiopathy is Related to a Mutation in the Cystatin C Gene, An Inhibitor of Cysteine Proteases" May 1989, J. Exp. Med. 169(5):1771-1778.
Liang et al. "Oxidative stress-induced mitochondrial DNA damage in human retinal pigment epithelial cells: a possible mechanism for RPE aging and age-related macular degeneration" Apr. 1, 2003, Exp. Eye Res. 76(4):397-403.
Lieberman et al. "Clinical evaluation of pramipexole in advanced Parkinson's disease: Results of a double-blind, placebo-controlled, parallel-group study" 1997, Neurology 49:162-168.
Lieberman et al. "Pharmaceutical Dosage Forms: Disperse Systems" 1996, Marcel Dekker, Inc., New York vol. 2 (TOC).
Lieberman et al. "Pharmaceutical Dosage Forms: Tablets" 1989, Marcel Dekker, Inc., New York vol. 1 (TOC).
Lin et al. "Large-scale protein identification using mass spectrometry" 2003, Biochimica et Biophysica Acta 16460(2):1-10.
Lofberg, et al. "Immunohistochemical characterization of the amyloid deposits and quantitation of pertinent cerebrospinal fluid proteins in hereditary cerebral hemorrhage with amyloidosis" Mar.-Apr. 1987, Stroke 18(2):431-440.
Lomen-Hoerth "Amyotrophic lateral sclerosis from bench to bedside" 2008, Semin. Neurol. 28(2):205-211.
Love "Oxidative Stress in Brain Ischemia" Apr. 5, 1999, Brain Pathology 9(1)119-131 (Abstract).
Malaspina et al. "Differential expression of 14 genes in amyotrophic lateral sclerosis spinal cord detected using gridded eDNA arrays" 2001, J. Neurochemistry 77(1):132-145.
Martens "Cloning and Sequence Analysis of Human Pituitary eDNA Encoding the Novel Polypeptide 7B2" Jul. 1988, FEBS Letters 234(1):160-164.
Martens et al. "The novel pituitary polypeptide 7B2 is a highly-conserved protein coexpressed with proopiomelanocortin" Apr. 1989, Eur. J. Biochem. 181(1):75-79.
Matthews et al. "Assessment of the Health Effects of Chemicals in Humans: I. QSAR Estimation of the Maximum Recommended Therapeutic Dose (MRTD) and No Effect Level (NOEL) of Organic Chemicals Based on Clinical Trial Data" 2004, Current Drug Discovery Technologies 1:61-76.
Mbikay et al. "Neuroendocrine secretory protein 7B2: structure, expression and functions" Jul. 15, 2001, Biochem. J. 357(2):329-342.
Menzies et al. "Mitochondrial dysfunction in a cell culture model of familial amyotrophic lateral sclerosis" Jul. 2002, Brain 125(7):1522-1533.
Merck Manuals Online Medical Library, Age-Related Macular Degeneration (ARMD), 2005, printed Aug. 13, 2008 from http://www.merck.com/mmpe/print/sec09/ch106/ch106b.html, 2 pages.
Mey et al. "Retinoic acid signaling in the nervous system of adult vertebrates" 2004, Neuroscientist 10(5):409-421.
Mhatre et al. "Oxidative Stress and Neuroinflammation in Alzheimer's Disease and Amyotrophic Lateral Sclerosis; Common Links and Potential Therapeutic Targets" Apr. 2004, J. Alzheimers Dis. 6(2):147-157 (abstract only).
Mierau et al. "Pramipexole binding and activation of cloned and expressed dopamine $D_2$, $D_3$ and $D_4$ receptors" 1995, Eur. J. Pharmacol. 290:29-36.
Miklya et al. "A pharmacological analysis elucidating why, in contrast to (−)-deprenyl (selegiline), α-tocopherol was ineffective in the DATATOP study" 2003, Life Sciences 72:2641-2648.
Mirapex® Prescribing Information from Boehringer Ingelheim, 2006, http://www.biopsychiatry.com/pramipexole-mirapex.pdf (retrieved May 10, 2012).
Moore et al. "An Efficient and Operationally Convenient General Synthesis of Tertiary Amines by Direct Alkylation of Secondary Amines with Alkyl Halides in the Presence of Huenig's Base" 2005, ARKIVOC 6:287-292.
Nagai et al. "Rats expressing human cytosolic copper-zinc superoxide dismutase transgenes with amyotrophic lateral sclerosis: associated mutations develop motor neuron disease" Dec. 1, 2001, J. Neurosci. 21(23):9246-9254.

(56) References Cited

OTHER PUBLICATIONS

Nilsen et al. "Mitochondria as Therapeutic Targets of Estrogen Action in the Central Nervous System" Aug. 2004, Curr. Drug Targets—CNS Neurol. Disord. 3(4):297-313.
Ong et al. "An Evaluation of the Use of Two-Dimensional Gel Electrophoresis in Proteomics" 2001, Biomolecular Engineering 18(5):195-205.
Palliative (n.d.) The American Heritage® Stedman's Medical Dictionary, Retrieved Jun. 12, 2009, from Dictionary.com website: http://dictionary.reference.com/browse/palliative.
Paquet et al. "The neuroendocrine precursor 7B2 is a sulfated protein proteolytically processed by a ubiquitous furin-like convertase" Jul. 29, 1994, J. Biol. Chem. 269(30):19279-19285.
Pattee et al. "Reduction of oxidative stress in amyotrophic lateral sclerosis following pramipexole treatment" Jan. 2003, Amyotrophic Lateral Sclerosis and Other Motor Neuron Disorders 4(2):90-95 (abstract).
Paulson "Protein Fate in Neurodegenerative Proteinopathies: Polyglutamine Diseases Join the (Mis) Fold" 1999, Am. J. Hum. Genet. 64(2):339-345.
Petersen et al. "Impaired Mitochondrial Activity in the Insulin-Resistant Offspring of Patients with Type 2 Diabetes" 2004, New England Journal of Medicine 350:664-671.
Piercey et al. "Excitation of type II anterior caudate neurons by stimulation of dopamine $D_3$ receptors" 1997, Brain Research 762:19-28.
Piercey et al. "Inhibition of dopamine neuron firing by pramipexole, a dopamine $D_3$ receptor-prefering agonist: comparison to other dopamine receptor agonists" 1996, European J. of Pharmac. 312:35-44.
Public Statement on Mirapex, Sudden Onset of Sleep from the European Agency for the Evaluation of Medicinal Products (EMEA), Jul. 19, 1999, www.emea.europa.eu/pdfs/human/press/pus/2064299.pdf.
Ranganathan et al, "Proteomic profiling of cerebrospinal fluid identifies biomarkers for amyotrophic lateral sclerosis" Dec. 2005, J. Neurochem. 95(5):1461-1471.
Robberecht "Oxidative Stress in Amyotrophic Lateral Sclerosis" 2000, J. Neurol. 247(1):11-16 (abstract).
Rowland et al. "Amyotrophic Lateral Sclerosis" May 2001, N Eng Journal of Medicine, 344:1688-1700.
Ryberg et al. "Discovery and Verification of Amyotrophic Lateral Sclerosis Biomarkers by Proteomics" Jul. 2010, Muscle & Nerve 42(1):104-111.
Sanchez et al. "Cystatin C as a potential cerebrospinal fluid marker for the diagnosis of Creutzfeldt-Jakob disease" 2004, Proteomics 4(8):2229-2233.
Sayeed et al. "Patch Clamp Reveals Powerful Blockade of the Mitochondrial Permeability Transition Pore by the D2-Receptor Agonist Pramipexole" 2006, FASB Journal 20:556-558.
Schilling et al. "Neuroendocrine and side effect profile of pramipexole, a new dopamine receptor agonist, in humans" 1992, Clin. Pharmacol. Ther. 51:541-548.
Schmidt et al. "Neurodegenerative diseases of the retina and potential for protection and recovery" Jun. 2008 (printed from http://www.nncbi.nim.nih.gov/pubmed/19305795?dopt_Abstract) Curr. Neuropharmacol. 6(2) (Abstract, 1 page).
Schneider et al. "Dopamine Autoreceptor Agonists: Resolution and Pharmacological Activity of 2,6-Diaminotetrahydrobenzothiazole and an Aminothiazole Analogue of Apomorphine" 1987, *J. Med. Chem.* 30:494-498.
Schuelke et al. "Myostatin Mutation Associated Wth Gross Muscle Hypertrophy in a Child" 2004, N. Engl. J. Med. 350:2682-2688 (Para.1).
Shannon et al. "Efficacy of Pramipexole, a Novel Dopamine Agonist, as Monotherapy in Mild to Moderate Parkinson's Disease" 1997, Neurology 49(3)a;724-728.
Sousa et al. "Deposition of transthyretin in early stages of familial amyloidotic polyneuropathy: evidence for toxicity of nonfibrillar aggregates" Dec. 2001, Am. J. Pathol. 159(6):1993-2000.
Sousa et al. "Evidence for early cytotoxic aggregates in transgenic mice for human transthyretin Leu55Pro" Nov. 2002, Am. J. of Pathol. 161(5):1935-1948.
Stein et al. "Neutralization of transthyretin reverses the neuroprotective effects of secreted amyloid precursor protein (APP) in APPsw mice resulting in tau phosphorylation and loss of hippocampal neurons: Support for the amyloid hypothesis" Sep. 1, 2004, J. Neurosci. 24(35):7707-7717.
The Foundation Fighting Blindness "Animal Models for Studying Inherited Degenerative Retinal Disease" 2000 (printed from www.retina-international.org/sci-news/animmod.doc_on_1/11/2009) The Foundation Fighting Blindness (23 pages).
Tombran-Tink et al. "Neuroprotection in Macular Degeneration" 2005, Age-Related Macular Degeneration: A Comprehensive Textbook (Lippincott Williams & Wilkins), 29:335-336.
Tsuzuki et al. "Structure of the Human Prealbumin Gene" Oct. 5, 1984, J. Biol. Chem. 260(22):12224-12227.
U.S. Dept. of HHS FDA CDER (Guidance for Industry), Jul. 2005, 30 pp.
Voskoglou-Nomikos et al. (Clinical Predictive Value of the in Vitro Cell Line, Human Xenograft, and Mouse Allograft Preclinical Cancer Models; Clinical Cancer Research; vol. 9: 4227-4239; Sep. 15, 2003).
Wang et al. "R+ pramipexole as a mitochondrially focused neuroprotectant: initial early phase studies in ALS" Feb. 2008, Amyotroph Lateral Scler. 9(1):50-58. PubMed PMID: 18270879.
Wedi et al. "Chronic urticarial serum induces histamine release, leukotriene production, and basophil CD63 surface expression-inhibitory effects of anti-inflammatory drugs" Journal of allegery and clinical immunology, Mar. 2000, 105(3):552-560.
Winkler et al. "Oxidative damage and age-related macular degeneration" Nov. 3, 1999, Mol. Vis. 5:32 (Abstract).
Wong "A 384-well cell-based phosphor-ERK assay for dopamine D2 and D3 receptors" 2004, Analytical Biochem. 333:265-272.
Wong et al. "Activation of Extracellular Signal-Regulated Kinase by Dopamine D2 and D3 Receptors" 2003, Society for Neuroscience Abstracts (retrieved on line at sfn.scholarone.com/itin2003/main.html?new_page_id=126&abstract_id=3866&p_num=363.4&is_tech=0 on Jun. 23, 2008).
Worker "Novel Therapeutic Strategies" 1999, IDrugs, Current Drugs Ltd, GB 2(9):848-852 XP000972503.
Wright et al. "Influence of Probenecid (PR) and Cimetidine (C) on Pramipexole (PX) Pharmacokinetics" Feb. 1995, Clin. Pharmacol. & Ther. 59(2):PII-99 (abstract).
Written Opinion of International Search Authority dated Aug. 15, 2005 for PCT/US2006/031831.
Zheng et al. "Purification and identification of an estrogen binding protein from rat brain: oligomycin sensitivity-conferring protein (OSCP), a subunit of mitochondrial F0F1-ATP synthase/ATPase" Jan. 1999, J. Ster. Biochem. Mol. Biol. 68(1-2):65-75.
B.R. Brooks, "EI Escorial World Federation of Neurology Criteria for the Diagnosis of Amyotrophic Lateral Sclerosis", 1994, Journal of the Neurological Sciences, vol. 124, Suppl., pp. 96-107.
Brooks, et al., "EI Escorial revisited: Revised criteria for the diagnosis of amyotrophic lateral sclerosis", 2000, ALS and other motor neuron disorders, vol. 1, pp. 293-299.
Cudkowicz et al., "The effects of dexpramipexole (KNS-760704) in individuals with amyotrophic lateral sclerosis", Dec. 2011, Nature Medicine, vol. 17, No. 12, pp. 1652-1656; Supplemental Materials included with total of 27 pages.
Rudnicki et al., "Dexpramipexole effects on functional decline and survival in subjects with amyotrophic lateral sclerosis in a Phase II study: Subgroup analysis of demographic and clinical characteristics", Feb. 1, 2013, Amyotrophic Lateral Sclerosis and Frontotemporal Degeneration, vol. 14, pp. 44-51.
National Institutes of Health/ U.S. National Library of Medicine, "Creatine phosphokinase test", Updated Jan. 9, 2015, URL of this page: //www.nlm.nih.gov/medlineplus/ency/article/003503.htm, pp. 1-4.
International Search Report and Written Opinion for PCT/US2016/22067 dated Jun. 3, 2016.
PDF regarding ALS from Florida Hospital, retrieved on Jul. 12, 2018.

SYNTHESIS OF AMINE SUBSTITUTED 4,5,6,7-TETRAHYDROBENZOTHIAZOLE COMPOUNDS

CROSS REFERENCE TO RELATED APPLICATIONS

The present application is a continuation of U.S. patent application Ser. No. 14/366,590, Jun. 18, 2014, now U.S. Pat. No. 9,512,096, which is a U.S. national stage filing under 35 U.S.C. § 371 of International Application No. PCT/US2012/071335 filed Dec. 21, 2012 which claims priority to U.S. Provisional Application Ser. No. 61/579,188, filed on Dec. 22, 2011, the disclosure of which is incorporated herein by reference in its entirety.

TECHNICAL FIELD OF THE INVENTION

The present invention is related to an improved process for the preparation of amino-substituted 4,5,6,7-tetrahydrobenzothiazole compounds of formula I, such as the compound 2-amino-4,5,6,7-tetrahydro-6-(n-propylamino)benzothiazole. The invention further relates to an improved synthesis of (R)-2-amino-4,5,6,7-tetrahydro-6-(n-propylamino)benzothiazole. The invention also relates to the methods and intermediates associated with the synthetic process.

BACKGROUND OF THE INVENTION

The compound 2-amino-4,5,6,7-tetrahydro-6-(n-propylamino)benzothiazole is a synthetic aminobenzothiazole derivative whose (6S) enantiomer, commonly known as pramipexole and commercially available under the Mirapex® name, is a potent dopamine agonist and thus mimics the effects of the neurotransmitter, dopamine. The (6R) enantiomer, (R)-(+)-2-amino-4,5,6,7-tetrahydro-6-(n-propylamino)benzothiazole, or "dexpramipexole," is an effective mitochondria-targeted neuroprotectant that exhibits excellent anti-oxidative properties, and is currently undergoing clinical development for the treatment of amyotrophic lateral sclerosis (ALS).

Synthetic procedures to produce pramipexole/dexpramipexole have been described in patent and non-patent literature. For example, one synthetic process for the preparation of pramipexole is accomplished via reductive amination of propanal with 2,6-diamino-4,5,6,7-tetrahydrobenzothiazole. Another preparation of pramipexole and dexpramipexole has also been described, where propionic anhydride and 2,6-diamino-4,5,6,7-tetrahydrobenzothiazole are combined to form the amide intermediate, 2-amino-6-propanoylamino-4,5,6,7-tetrahydrobenzothiazole, which is then reduced to pramipexole/dexpramipexole. Unfortunately, the syntheses described above are not suitable for industrial scale preparation as the hydride reducing reagents involved are inherently dangerous and often toxic.

As described in the literature, racemic 2,6-diamino-4,5,6,7-tetrahydrobenzothiazole can be enantiomerically purified by selective crystallization of the acid addition salt using an optically active acid, such as tartaric acid, followed by neutralization to the free, enantiomerically enriched diamine product. However, this method has limitations as to the optical purity of the resulting 2,6-diamino-4,5,6,7-tetrahydrobenzothiazole product, with typical maximum optical purities of about 98%-99% ee.

Described herein is an improved synthesis of dexpramipexole using a procedure which includes direct alkylation of 2,6-diamino-4,5,6,7-tetrahydrobenzothiazole with n-propyl p-toluenesulfonate, followed by the formation of the dihydrochloride salt of dexpramipexole. The methods described herein provide increased yield and chemical purity as well as increased enantiomeric purity of the product. Additionally, the methods described herein provide a process which can be used on an industrial scale.

SUMMARY OF THE INVENTION

The present invention is related to an improved process for the preparation of amino-substituted 4,5,6,7-tetrahydrobenzothiazole compounds of formula I. In one aspect, the invention provides a process for preparing a compound of formula $I_{(HOTs)}$ formula $I_{(HOTs)}$

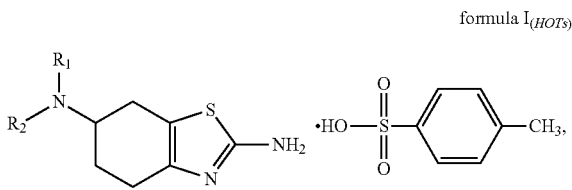

wherein $R_1$ and $R_2$ are each independently hydrogen or $C_{1-6}$ alkyl, wherein each $C_{1-6}$ alkyl is optionally and independently substituted with up to 3 occurrences of $C_{1-6}$ alkyl, aryl or heteroaryl;

the process comprises contacting a mixture, which comprises a compound of formula II formula II

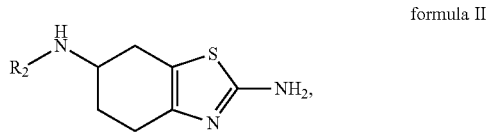

and a solvent, with a compound having the formula

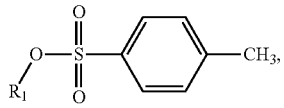

in the presence of a base, to provide compound of formula $I_{(HOTs)}$, wherein the solvent is acetonitrile, a mixture of acetonitrile and water, IPA, a mixture of IPA and water, a mixture of acetonitrile and IPA, or a mixture of acetonitrile, IPA and water.

In another aspect, the process includes the steps of:
a) forming a mixture comprising the compound of formula $I_{(HOTs)}$, IPA and water, and heating the mixture to a temperature from about 70° C. to about 85° C. (for example from about 72° C. to about 83° C., from about 75° C. to about 80° C. or about 78° C.);
b) cooling the mixture to a temperature from about −10° C. to about 15° C. (for example from about 0° C. to about 10° C., from about 3° C. to about 7° C. or about 5° C.); and
c) isolating the solid Compound $1_{(HOTs)}$ formed during step b.

In another aspect, the process comprises producing a compound of formula I formula I

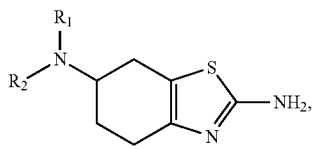

the process comprising the steps of:

a) forming a biphasic mixture comprising a compound of formula I$_{(HOTs)}$, 2-methyltetrahydrofuran and brine, wherein the brine has a salt content of about 2-20% (for example about 10-14%, about 11-13% or about 12%); and b) contacting the mixture with a base to produce a compound of formula I.

In another aspect, the process further comprises preparing a compound of formula I$_{(2HCl \cdot H2O)}$ formula I$_{(2HCl \cdot H2O)}$

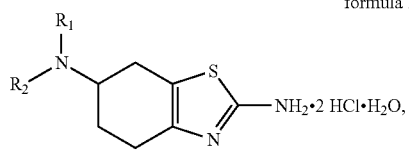

comprising the steps of:

a) forming a mixture comprising a compound of formula I, 2-methyltetrahydrofuran and IPA;

b) contacting the mixture with HCl; and c) isolating the solid compound of formula I$_{(2HCl \cdot H2O)}$ produced in step b.

In one aspect, the process comprises the steps of:

a) forming a mixture comprising a compound of formula I$_{(2HCl \cdot H2O)}$, IPA and water;

b) heating the mixture to a temperature from about 60° C. to about 90° C. (for example, from about 65° C. to about 85° C., from about 70° C. to about 82° C. or from about 75° C. to about 80° C.);

c) cooling the mixture to about 35-60° C. (for example, about 40-55° C., about 44° C. or about 50° C.);

d) removing water from the mixture;

e) cooling the solution to a temperature from about −10° C. to about 15° C. (for example, from about −5° C. to about 1° C. or from about 0° C. to about 5° C.); and f) isolating the solid compound of formula I$_{(2HCl \cdot H2O)}$.

In one aspect, the invention includes a process for preparing compound 1$_{(2HCl \cdot H2O)}$ Compound 1$_{(2HCl \cdot H2O)}$

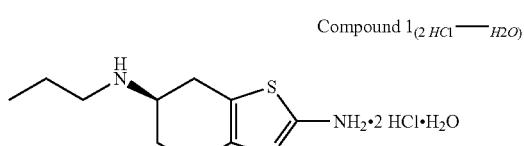

wherein the process comprises the steps of:

a) contacting a mixture comprising compound 2

Compound 2

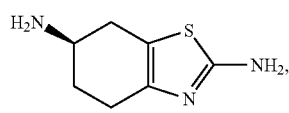

and a solvent, with n-PrOTs and DIPEA to provide Compound 1$_{(HOTs)}$

Compound 1$_{(HOTs)}$

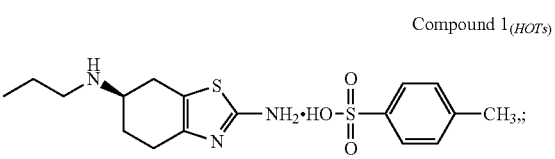

wherein the solvent is acetonitrile, a mixture of acetonitrile and water, IPA, a mixture of IPA and water, a mixture of acetonitrile and IPA, or a mixture of acetonitrile, IPA and water;

b) isolating the solid Compound 1$_{(HOTs)}$ formed in step a;

c) forming a mixture comprising Compound 1$_{(HOTs)}$, IPA and water, and heating the mixture to a temperature from about 70° C. to about 85° C. (for example from about 72° C. to about 83° C., from about 75° C. to about 80° C. or about 78° C.);

d) cooling the mixture to a temperature from about −10° C. to about 15° C. (for example from about 0° C. to about 10° C., from about 3° C. to about 7° C. or about 5° C.);

e) isolating the solid Compound 1$_{(HOTs)}$ formed in step d;

f) forming a biphasic mixture comprising Compound 1$_{(HOTs)}$, 2-methyltetrahydrofuran and brine, wherein the brine has a salt content of about 2-20% (for example about 10-14%, about 11-13% or about 12%);

g) contacting the mixture with sodium hydroxide to form Compound 1

Compound 1

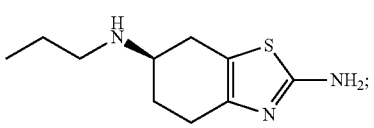

h) forming a mixture comprising Compound 1, 2-methyltetrahydrofuran and IPA;

i) contacting the mixture with HCl; and j) isolating the solid Compound 1$_{(2HCl \cdot H2O)}$ produced in step i.

In one aspect, the process comprises the steps of:

a) forming a mixture comprising Compound 1$_{(2HCl \cdot H2O)}$, IPA and water;

b) heating the mixture to a temperature from about 60° C. to about 90° C. (for example, from about 65° C. to about 85° C., from about 70° C. to about 82° C. or from about 75° C. to about 80° C.);

c) cooling the mixture to about 35-60° C. (for example, about 40-55° C., about 44° C. or about 50° C.);

d) removing water from the mixture;

e) cooling the solution to a temperature from about −10° C. to about 15° C. (for example, from about −5° C. to about 1° C. or from about 0° C. to about 5° C.); and f) isolating the solid Compound 1$_{(2HCl \cdot H2O)}$.

In one aspect, the solid Compound $1_{(2HCl-H2O)}$ isolated from the process is in the polymorphic Form A.

DETAILED DESCRIPTION OF THE FIGURES

DETAILED DESCRIPTION OF THE INVENTION

Definitions

Figure 1:
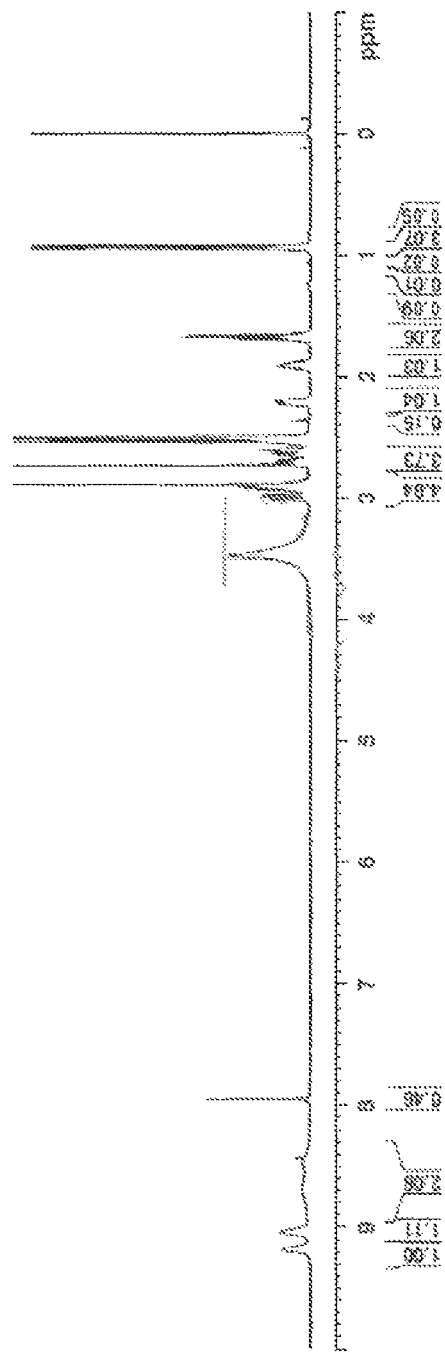
FIG. 1 is an $^1$H NMR (500 MHZ; DMSO-d$^6$) spectrum of Compound $1_{(2HCl-H2O)}$.

As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausolito: 1999, and "March's Advanced Organic Chemistry," 5th Ed., Ed.: Smith, M. B. and March, J., John Wiley & Sons, New York: 2001, the entire contents of which are incorporated herein by reference.

As used herein, "KF" is the Karl Fischer method of determining water content, which is determined by the Karl Fischer Titration (USP <921> Method 1a), described in detail herein.

As used herein, the term "brine" is an aqueous salt mixture, wherein the salt is soluble in water and comprises a metal atom having a +1 or +2 charge with one or two anions to balance the overall charge of the salt. Examples of acceptable salts for brine are, but are not limited to NaF, NaCl, NaBr, NaI, Na$_2$SO$_4$, NaHSO$_4$, Na$_2$CO$_3$, NaHCO$_3$, KF, KCl, KBr, KI, K$_2$SO$_4$, KHSO$_4$, K$_2$CO$_3$, KHCO$_3$, CaCl$_2$, CaBr$_2$, CaSO$_4$, CaCO$_3$, and the like. Acceptable brine solutions can contain from 1-50% salt by weight of the solution (for example about 2-20%, about 10-14%, about 11-13% or about 12%).

As used herein, the term "aliphatic" encompasses the terms alkyl, alkenyl, alkynyl.

As used herein, an "alkyl" group refers to a saturated aliphatic hydrocarbon group containing 1-8 (e.g., 1-6 or 1-4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of alkenyl groups include, but are not limited to allyl, isoprenyl, 2-butenyl, and 2-hexenyl.

As used herein, an "alkynyl" group refers to an aliphatic carbon group that contains 2-8 (e.g., 2-6 or 2-4) carbon atoms and at least one triple bond. Like an alkyl group, an alkynyl group can be straight or branched.

As used herein, an "amino" group refers to $-NR^XR^Y$ wherein each of $R^X$ and $R^Y$ is independently hydrogen, alkyl, cycloalkyl, (cycloalkyl)alkyl, aryl, aralkyl, heterocycloalkyl, (heterocycloalkyl)alkyl, heteroaryl, or carbonyl. Examples of amino groups include alkylcarbonylamino, alkylsulfonylamino, alkoxycarbonylamino, (azacycloalkylcarbonyl)amino, heteroaralkylcarbonylamino, heteroarylcarbonylamino, carbonylamino, (heterocycloalkyl)carbonylamino, (heterocycloalkyl)alkylcarbonylamino, heteroarylcarbonylamino, arylcarbonylamino, aralkylcarbonylamino, (cycloalkyl)alkylcarbonylamino, cycloalkylcarbonylamino. When the term "amino" is not the terminal group (e.g., alkylcarbonylamino), it is represented by $-NR^X-$. $R^X$ has the same meaning as defined above. Examples of possible $R^X$ and $R^Y$ include, but are not limited to sulfonylamino, alkylamino, carbonylamino, carboxy, oxo, hydroxyl, sulfo, mercapto, alkylsulfanyl, alkylsulfinyl, alkylsulfonyl, aminocarbonyl, alkylcarbonyl, cycloalkylcarbonyl, cycloalkylalkylcarbonyl, arylcarbonyl, aralkylcarbonyl, heterocycloalkylcarbonyl, heterocycloalkylalkylcarbonyl, heteroarylcarbonyl, or heteroaralkylcarbonyl.

As used herein, a "carbonyl" group, when used alone or as part of another structure refers to $-(CO)R^X$, where $R^X$ is defined above. When the term "carbonyl" is not the terminal group (e.g., arylaminoalkylcarbonyl) it is represented by $-C(O)R^X$. Without limitation, carbonyl groups can include optionally substituted aminocarbonyl, alkoxyalkoxycarbonyl, alkylaminocarbonyl, arylcarbonyl (e.g., haloarylcarbonyl), heterocycloalkylcarbonyl, heterocycloalkenylcarbonyl, arylaminocarbonyl (e.g., haloarylaminocarbonyl), cyanoalkylarylcarbonyl, heterocycloalkoxycarbonyl, alkynyloxycarbonyl, cycloalkoxycarbonyl, heterobicycloarylcarbonyl, alkylheteroarylaminocarbonyl, alkoxyarylcarbonyl (e.g., haloalkoxyarylcarbonyl), (alkylheterocyclo)alkenylcarbonyl, heteroarylcarbonyl, arylcarbonyl, heteroarylcarbonyl, alkoxycarbonyl (e.g., haloalkoxycarbonyl), alkylarylcarbonyl, cycloalkylcarbonyl, alkylheteroarylcarbonyl, arylsulfonylcarbonyl, aminocarbonyl, sulfonylcarbonyl, alkylcarbonyl, alkylsulfonylcarbonyl, alkylcarbonyl, arylaminocarbonyl, or the like.

As used herein, an "aryl" group used alone or as part of a larger moiety as in "aralkyl", "aralkoxy", or "aryloxyalkyl" refers to an aromatic monocyclic (e.g., phenyl); an aromatic bicyclic (e.g., indenyl, naphthalenyl, tetrahydronaphthyl, tetrahydroindenyl); an aromoatic tricyclic (e.g., fluorenyl, tetrahydrofluorenyl, anthracenyl, or tetrahydroanthracenyl); or a benzofused group having 2-3 carbocyclic rings in which one or more of the rings are aromatic. For example, a benzofused group includes phenyl fused with two or more C$_{4-8}$ carbocyclic moieties.

A "heteroaryl" group, as used herein, refers to a monocyclic, bicyclic, or tricyclic ring structure having 4 to 15 ring atoms wherein one or more of the ring atoms is a heteroatom (e.g., N, O, S, or combinations thereof) and wherein one or more rings of the bicyclic or tricyclic ring structure is aromatic. A heteroaryl group includes a benzofused ring system having 2 to 3 rings. For example, a benzofused group includes benzo fused with one or two C$_{4-8}$ heterocyclic moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are azetidinyl, pyridyl, 1H-indazolyl, furyl, pyrrolyl, thienyl, thiazolyl, oxazolyl, imidazolyl, tetrazolyl, benzofuryl, isoquinolinyl, benzthiazolyl, xanthene, thioxanthene, phenothiazine, dihydroindole, benzo[1,3]dioxole, benzo[b]furyl, benzo[b]thiophenyl, indazolyl, benzimidazolyl, benzthiazolyl, puryl, cinnolyl, quinolyl, quinazolyl, cinnolyl, phthalazyl, quinazolyl, quinoxalyl, isoquinolyl, 4H-quinolizyl, benzo-1,2,5-thiadiazolyl, or 1,8-naphthyridyl.

Without limitation, monocyclic heteroaryls include furyl, thiophenyl, 2H-pyrrolyl, pyrrolyl, oxazolyl, thazolyl, imidazolyl, pyrazolyl, isoxazolyl, isothiazolyl, 1,3,4-thiadiazolyl, 2H-pyranyl, 4-H-pranyl, pyridyl, pyridazyl, pyrimidyl, pyrazolyl, pyrazyl, or 1,3,5-triazyl. Monocyclic heteroaryls are numbered according to standard chemical nomenclature. For instance:

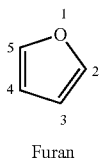 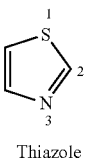 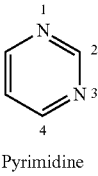

Furan  Thiazole  Pyrimidine

Without limitation, bicyclic heteroaryls include indolizyl, indolyl, isoindolyl, 3H-indolyl, indolinyl, benzo[b]furyl, benzo[b]thiophenyl, quinolinyl, tetrahydroquinolinyl, isoquinolinyl, tetrahydroisoquinolinyl, indolizyl, isoindolyl, indazolyl, benzimidazyl, benzthiazolyl, purinyl, 4H-quinolizyl, quinolyl, isoquinolyl, cinnolyl, phthalazyl, quinazolyl, quinoxalyl, 1,8-naphthyridyl, indolizinyl, imidazopyridinyl, tetrahydrobenzoazepinyl, tetrahydrobenzooxazepinyl, benzo[1,4]oxazinyl, benzodihydro[1,4]oxazinyl, benzo[1,3]oxazinyl, benzodihydro[1,3]oxazinyl, fused pyrido[1,4]oxazinyl, fused pyrido[1,3]oxazinyl, fused pyrido[1,4]dihydrooxazinyl, fused pyrido[1,3]dihydrooxazinyl, fused pyrimido[1,4]oxazinyl, fused pyrimido[1,3]oxazinyl, fused pyrimido[1,4]dihydrooxazinyl, fused pyrimido[1,3]dihydrooxazinyl, fused pyrizo[1,4]oxazinyl, fused pyrizo[1,3]oxazinyl, fused pyrizo[1,4]dihydrooxazinyl or fused pyrizo[1,3]dihydrooxazinyl or pteridyl. Bicyclic heteroaryls are numbered according to standard chemical nomenclature. For instance:

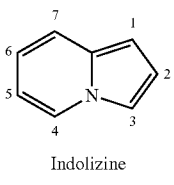 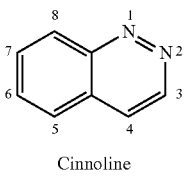

Indolizine  Cinnoline

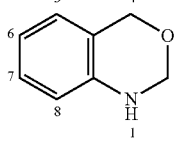 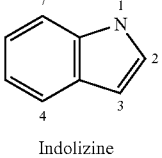

3,1-Benzoxazine  Indolizine

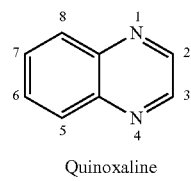

Quinoxaline

As used herein, a "halogen" or "halo" group refers to fluorine, chlorine, bromine or iodine.

As used herein, a "haloaliphatic" group refers to an aliphatic group substituted with 1-3 halogen. For instance, the term haloalkyl includes the group —CF$_3$.

As used herein, a "sulfamoyl" group refers to the structure —S(O)$_2$—NR$^y$R$^y$ or —NR$^x$—S(O)$_2$—R$^z$ wherein R$^x$, R$^y$, and R$^z$ have been defined above.

As used herein, a "sulfamide" group refers to the structure —NR$^x$—S(O)$_2$—NR$^y$R$^z$ wherein R$^x$, R$^y$, and R$^z$ have been defined above.

As used herein, a "carbonylamino" group used alone or in connection with another group refers to an amido group such as R$^x$—C(O)—NR$^x$—. For instance an alkylcarbonylamino includes alkyl-C(O)—NR$^x$—, wherein R$^x$ has been defined above.

As used herein, a "aminocarbonyl" group used alone or in connection with another group refers to an amido group such as N(R$^x$)$_2$—C(O)—.

As used herein, an "alkoxycarbonyl" used alone or in connection with another group refers to a carbonyl group such as alkyl-O—C(O)—.

As used herein, an "alkoxyalkyl" refers to an alkyl group such as alkyl-O-alkyl-, wherein alkyl has been defined above.

As used herein, an "aminocarbonyl" refers to an amido group such as —NR$^x$—C(O)—, wherein R$^x$ has been defined above.

As used herein, an "aminosulfonyl" refers to the structure —N(R$^x$)$_2$—S(O)$_2$—, wherein R$^x$ has been defined above.

As used herein, an "oxo" refers to =O.

As used herein, an "aminoalkyl" refers to the structure N(R$^x$)$_2$-alkyl-.

As used herein, a "cyanoalkyl" refers to the structure -alkyl-(CN).

As used herein, an "alkylsulfonyl" group refers to the structure alkyl-S(O)$_2$—.

As used herein, a "sulfonylamino" group refers to the structure R$^x$—S(O)$_2$—N(R$^x$)$_2$—, wherein R$^x$ has been defined above.

As used herein, IPA stands for "isopropanol" or "isopropyl alcohol." As used herein, DIPEA stands for "diisopropylethylamine" or "hunig's base." As used herein, TEA stands for "triethylamine." As used herein, 2-MeTHF stands for "2-methyltetrahydrofuran." As used herein, IPOAc stands for "isopropyl acetate." As used herein, DCM stands for "dichloromethane." As used herein, n-PrOTs stands for "n-propyltolsylate" or "n-propyl-p-toluenesulfonate"

As used herein, pictured substituents drawn with a single, unattached wavy line drawn perpendicular to a bond of the substituent is meant to show the attachment point of the substituent. For example, the pyrrole substituent,

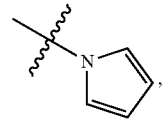 [SMILES: *n1cccc1]

is shown as attached to the main core structure by the ring nitrogen, while the pyrrole substituent,

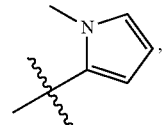 [SMILES: *c1cccn1C]

is shown as attached to the main core structure by the carbon atom adjacent to the ring nitrogen.

As used herein, pictured ring structures drawn with a substituent's bond overlayed on one of the ring bonds shows that the substituent can be at any substitutable atom of the entire ring structure, whether the ring structure is monocyclic or multicyclic. For example, the R substituent on the structure,

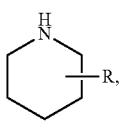

can be substituted on any atom of the piperidine ring, and the R substituent on the structure,

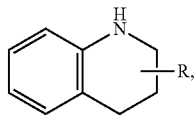

can be substituted on any atom of the benzene ring or piperidine ring.

As used herein, pictured structures having methyl substituents are drawn to show those methyl substituents as an external bond. Specifically, the structure,

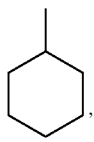

is identical to the structure

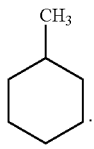

As depicted herein, divalent substituents, such as an amide, shown as —C(O)N($R^X$)—, are meant to include the substituent in both directions. For example, the generic structure

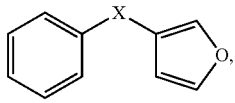

wherein X is an unsubstituted amide can be

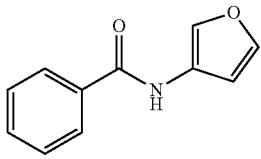 [SMILES: O=C(Nc1ccoc1)c1ccccc1]

or

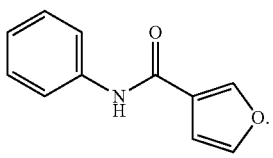 [SMILES: O=C(Nc1ccccc1)c1ccoc1]

Some examples of generic divalent substituents include, but not limited to —CO—, —CS—, —CONR$^X$—, —CO$_2$—, —OCO—, —NR$^X$—, —NR$^X$CO$_2$—, —O—, —NR$^X$CONR$^X$—, —OCONR$^X$—, —NR$^X$CO—, —S—, —SO—, —SO$_2$—, —SO$_2$NR$^X$—, —NR$^X$SO$_2$—, and —NR$^X$SO$_2$NR$^X$—.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group may have a substituent at each substitutable position of the group, and when more than one position in any given structure may be substituted with more than one substituent selected from a specified group, the substituent may be either the same or different at every position. A ring substituent, such as a heterocycloalkyl, may be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, the replacement of a carbon by a $^{13}$C- or $^{14}$C-enriched carbon, the replacement of a sulfur by a $^{33}$S or $^{35}$S enriched sulfur, or the replacement of nitrogen by $^{15}$N or $^{16}$N enriched nitrogen are within the scope of this invention. Such compounds are useful, for example, as analytical tools or probes in biological assays.

Embodiments of the Invention

In one aspect, the invention provides a process for preparing a compound of formula $I_{(HOTs)}$ formula I$_{(HOTs)}$

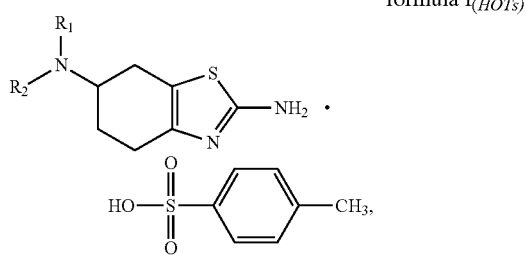

wherein R$_1$ and R$_2$ are each independently hydrogen or C$_{1-6}$ alkyl, wherein each C$_{1-6}$ alkyl is optionally and independently substituted with up to 3 occurrences of C$_{1-6}$ alkyl, aryl or heteroaryl;

the process comprises contacting a mixture, which comprises a compound of formula II

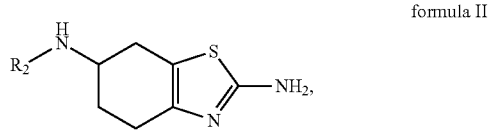

and a solvent, with a compound having the formula

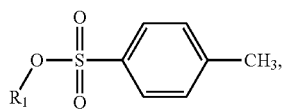

in the presence of a base, to provide compound of formula I$_{(HOTs)}$, wherein the solvent is acetonitrile, a mixture of acetonitrile and water, IPA, a mixture of IPA and water, a mixture of acetonitrile and IPA, or a mixture of acetonitrile, IPA and water.

In one embodiment of this aspect, the solvent is acetonitrile. In a further embodiment, the solvent is a mixture of acetonitrile and water. In another embodiment, the solvent is IPA. In a further embodiment, the solvent is a mixture of IPA and water. In another embodiment, the solvent is a mixture of acetonitrile and IPA. In a further embodiment, the solvent is a mixture of acetonitrile, IPA and water.

In one embodiment, the solvent is a mixture of acetonitrile, IPA and water, and the resulting product compound of formula I$_{(HOTs)}$ is obtained at a higher yield compared to the same process using other solvent systems. In one embodiment, the yield is greater than 70%. In another embodiment, the yield is greater than 80%. In still another embodiment, the yield is greater than 83%. In a further embodiment, the yield is about 83.8%. In another embodiment, the solvent is a mixture of acetonitrile, IPA and water, and the resulting product compound of formula I$_{(HOTs)}$ is obtained in a more purified state compared to the same process using other solvent systems. In one embodiment, the chemical purity of the product is greater than 95%. In another embodiment, the chemical purity of the product is greater than 97%. In another embodiment, the chemical purity of the product is greater than 98%. In another embodiment, the chemical purity of the product is greater than 98.5%. In another embodiment, the chemical purity of the product is about 98.74%.

In another aspect, the process includes the steps of:
a) forming a mixture comprising the compound of formula I$_{(HOTs)}$, IPA and water, and heating the mixture to a temperature from about 70° C. to about 85° C. (for example from about 72° C. to about 83° C., from about 75° C. to about 80° C. or about 78° C.);
b) cooling the mixture to a temperature from about −5° C. to about 15° C. (for example from about 0° C. to about 10° C., from about 3° C. to about 7° C. or about 5° C.); and
c) isolating the solid Compound 1$_{(HOTs)}$ formed during step b.

In some embodiments, R$_2$ is hydrogen. In some embodiments, R$_2$ is C$_{1-6}$ alkyl. In some embodiments, R$_2$ is methyl, ethyl, isopropyl, n-propyl or benzyl. In some embodiments, R$_1$ is C$_{1-6}$ alkyl. In another embodiment, R$_1$ is methyl, ethyl, isopropyl, n-propyl, n-butyl, isobutyl, t-butyl, pentyl, hexyl, benzyl, chlorobenzyl, bromobenzyl, nitrobenzyl or 2-phenylethyl. In a further embodiment, R$_1$ is n-propyl.

In some further embodiments, the stereochemistry of the carbon atom to which the —NR$_1$(R$_2$) moiety is attached is in the (R) configuration. In another further embodiment, the stereochemistry of the carbon atom to which the —NR$_1$(R$_2$) moiety is attached is in the (S) configuration.

In some embodiments, the base is triethylamine, DIPEA, pyridine or DBU. In other embodiments, the base is DIPEA. In other embodiments, the base is triethylamine. In other embodiments, the base is pyridine.

In one embodiment the process comprises contacting a mixture, which comprises a compound of formula II

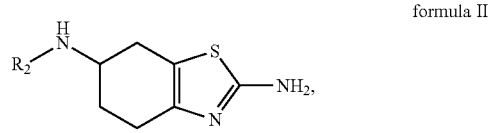

and a solvent, with a compound having the formula

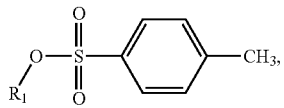

in the presence of a base, to provide compound of formula I$_{(HOTs)}$, wherein the solvent is acetonitrile, a mixture of acetonitrile and water, IPA, a mixture of IPA and water, a mixture of acetonitrile and IPA, or a mixture of acetonitrile, IPA and water. In one embodiment of this aspect, the solvent is acetonitrile. In a further embodiment, the solvent is a mixture of acetonitrile and water. In another embodiment, the solvent is IPA. In a further embodiment, the solvent is a mixture of IPA and water. In another embodiment, the solvent is a mixture of acetonitrile and IPA. In a further embodiment, the solvent is a mixture of acetonitrile, IPA and water.

In some embodiments, water is present from about 0% to about 10% by weight in the mixture of acetonitrile and water. In some embodiments, the ratio of the mixture of acetonitrile to water is from about 3:1 wt/wt to about 200:1 wt/wt (for example from about 7:1 to about 79:1, from about 19:1 to about 49:1 or about 39:1). In another embodiment, the compound having the formula

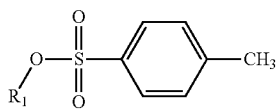

added to the mixture with rapid stirring. In another embodiment, the mixture comprising a compound of formula II, acetonitrile, water and a compound having the formula

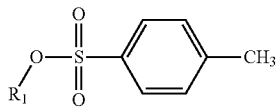

is heated to a temperature from about 60° C. to about 90° C. (for example, from about 65° C. to about 85° C., from about 68° C. to about 82° C. or from about 70° C. to about 80° C.). In another embodiment, the mixture comprising a Compound of formula II, acetonitrile, water and a compound having the formula

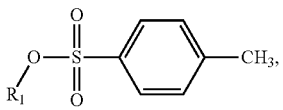

after being heated to a temperature from about 60° C. to about 90° C. (for example, from about 65° C. to about 85° C., from about 68° C. to about 82° C. or from about 70° C. to about 80° C.), is then stirred for about 6-16 hours (for example about 7-10 hours, about 8-10 hours, about 8-9 hours or about 9-10 hours).

In one embodiment, the solvent is a mixture of acetonitrile, IPA and water, and the resulting product compound of formula $I_{(HOTs)}$ is obtained at a higher yield compared to the same process using other solvent systems. In one embodiment, the yield is greater than 70%. In another embodiment, the yield is greater than 80%. In still another embodiment, the yield is greater than 83%. In a further embodiment, the yield is about 83.8%. In another embodiment, the solvent is a mixture of acetonitrile, IPA and water, and the resulting product compound of formula $I_{(HOTs)}$ is obtained in a more purified state compared to the same process using other solvent systems. In one embodiment, the chemical purity of the product is greater than 95%. In another embodiment, the chemical purity of the product is greater than 97%. In another embodiment, the chemical purity of the product is greater than 98%. In another embodiment, the chemical purity of the product is greater than 98.5%. In another embodiment, the chemical purity of the product is about 98.74%.

In one embodiment, the ratio of IPA to water in step a is from about 2.3:1 v/v to about 4.25:1 v/v (for example from about 2.5:1 to about 3.3:1 or about 3:1). In another embodiment, the mixture in step b is cooled over a period from about 2 hours to about 5 hours (for example from about 2.5 hours to about 4.5 hours, from about 2.8 hours to about 4.2 hours, from about 3 hours to about 4 hours, 3.25 hours, 3.5 hours or 3.75 hours). In some embodiments, the step of isolating the solid Compound $1_{(HOTs)}$ formed during step b is done using filtration. In some further embodiments, the filter cake is washed once or twice with 2 volumes of IPA.

In another aspect, the process includes producing a compound of formula I

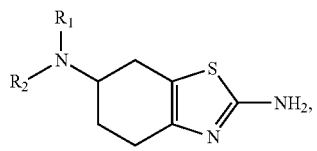

formula I the process comprising the steps of:
a) forming a biphasic mixture comprising a compound of formula $I_{(HOTs)}$, 2-methyltetrahydrofuran and brine, wherein the brine has a salt content of about 2-20% (for example about 10-14%, about 11-13% or about 12%); and
b) contacting the mixture with a base to produce a compound of formula I.

In one embodiment, the ratio of 2-methyltetrahydrofuran to brine in step a is from about 3:1 v/v to about 1:1 v/v (for example, from about 2.5:1 to about 1.5:1, from about 2:1 to about 1.6:1 or about 1.8:1).

In one embodiment, the base used in step b is sodium hydroxide, potassium hydroxide, sodium carbonate or potassium carbonate. In one further embodiment, the base is sodium hydroxide. In still a further embodiment, the sodium hydroxide is present in from about 1.0 molar equivalents to 5 molar equivalents (for example, about 1-4, about 1-3, about 1-2, about 1-1.5, about 1-1.25, about 1-1.10 or about 1.04 molar equivalents). In another embodiment, the base is added to the biphasic mixture with rapid stirring. In another embodiment, the base is added to the biphasic mixture as a 1.0 N-3.0 N solution, for example about a 2.0 N solution. In a further embodiment, the organic phase of the biphasic mixture comprising the product is used in the next step of the process without further purification of the product.

In another aspect, the process further comprises preparing a compound of formula $I_{(2HCl\text{-}H2O)}$ formula $I_{(2\ HCl\text{-}H2O)}$

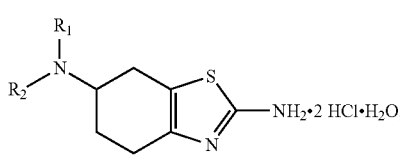

comprising the steps of:
a) forming a mixture comprising a compound of formula I, 2-methyltetrahydrofuran and IPA;
b) contacting the mixture with HCl; and
c) isolating the solid compound of formula $I_{(2HCl\text{-}H2O)}$ produced in step b.

In one embodiment, the ratio of 2-methyltetrahydrofuran to IPA in step a is from about 3:1 v/v to about 1:1 v/v (for example, from about 2.5:1 to about 1.5:1, from about 2:1 to about 1.6:1 or about 1.8:1).

In some embodiments, HCl in a solvent is added to the mixture comprising a compound of formula I, 2-methyltetrahydrofuran and IPA, in step b. In one further embodiment, the HCl solution is added with rapid stirring, for example 145 rpm. In another further embodiment, the HCl is added to the mixture as a solution in IPA. In still another further embodiment, the HCl solution is produced by diluting concentrated HCl with IPA to 5-10 times (for example 6-9 times, 7-8.5 times, 7.5-8.0 times, 7.7 times or 7.8 times) the original volume of concentrated HCl. In another embodiment, the HCl is present in an amount of about 2-4 (for example 2-3, 2-2.5, 2-2.2 or about 2.0) molar equivalents. In some embodiments, the final mixture is held at a temperature of about 20° C. prior to isolating the solid compound of formula $I_{(2HCl-H2O)}$. In one embodiment, the solid compound of formula $I_{(2HCl-H2O)}$ is isolated by filtration. In a further embodiment, the filter cake is washed once or twice with about 2 volumes of about 3-7 wt/wt % water in IPA or about 5 wt/wt % water in IPA.

In one aspect, the process comprises the steps of:
a) forming a mixture comprising a compound of formula $I_{(2HCl-H2O)}$, IPA and water;
b) heating the mixture to a temperature from about 60° C. to about 90° C. (for example, from about 65° C. to about 85° C., from about 70° C. to about 82° C. or from about 75° C. to about 80° C.);
c) cooling the mixture to about 35-60° C. (for example, about 40-55° C., about 44° C. or about 50° C.);
d) removing water from the mixture;
e) cooling the solution to a temperature from about −10° C. to about 15° C. (for example, from about −5° C. to about 1° C. or from about 0° C. to about 5° C.); and
f) isolating the solid compound of formula $I_{(2HCl-H2O)}$.

In one embodiment, the ratio of IPA to water in step a is from about 27:1 to about 2:1 (for example, from about 14:1 to about 4:1, from about 9.3:1 to about 6:1 or about 8:1). In one embodiment, the mixture is heated in step b over a time period of about 0.5-2 hours (for example, about 0.8-1.5 hours or about 1.0 hours). In a further embodiment, the heated mixture from step b is stirred for an additional 30-60 minutes.

In one embodiment, the mixture is cooled in step c over a time period of about 0.5-2 hours (for example, about 0.8-1.5 hours or about 1.0 hours). In a further embodiment, the mixture is stirred for an additional 25-35 minutes.

In one embodiment, water is removed from the mixture in step d by azeotropic distillation of IPA and water. In a further embodiment, the distillation is performed at reduced pressure. In still a further embodiment, the distillation is performed at a pressure from about 90 Torr to about 170 Torr (for example, from about 100 Torr to about 150 Torr, from about 110 Torr to about 130 Torr or from about 120 Torr to about 125 Torr). In another further embodiment, the pressure during distillation is ramped from about 140 Torr to about 160 Torr in the beginning of the distillation to from about 90 Torr to about 110 Torr at the end of the distillation (for example, about 150 Torr at the beginning of the distillation to about 100 Torr at the end of the distillation). In another further embodiment, IPA is added to the mixture during distillation. In some embodiments, the water content of the solution after performing step d is about 0-20% (for example, about 1-16%, about 2-14%, about 3-12%, about 4-10%, about 5-8%, about 5.5-6.5% or about 6%).

In a further embodiment, step d of the process further includes the steps of:
a) reducing the volume of the mixture by distillation at reduced pressure;
b) diluting the mixture with IPA; and
c) optionally repeating steps a and b one or more times.

In one further embodiment, the water content of the resulting mixture is about 3-10%.

In one embodiment, the process further comprises the step of adding a specific volume of IPA to the mixture to produce a final water content in the supernatant portion of the mixture of about 6%, wherein the specific volume of IPA is determined by performing the calculation: Final volume (mL) of IPA to be added to the mixture=((24×KF×S)/(1−6.5×KF))−(2.4×KF), wherein "KF" is the water content as determined by the Karl Fischer method, and "S" is the weight in grams of starting compound of formula $I_{(2HCl-H2O)}$.

In one aspect, the invention includes a process for preparing compound $1_{(2HCl-H2O)}$

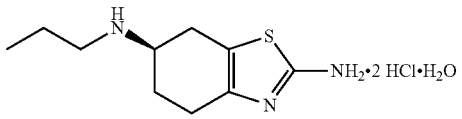

Compound $1_{(2\ HCl\cdot H2O)}$ wherein the process comprises the steps of:
a) contacting a mixture comprising compound 2

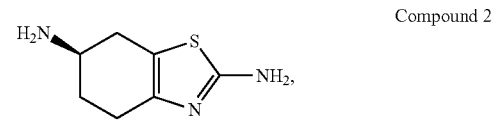 [SMILES: Nc1nc2c(s1)C[C@H](N)CC2]

Compound 2 and a solvent, with n-PrOTs and DIPEA to provide Compound $1_{(HOTs)}$

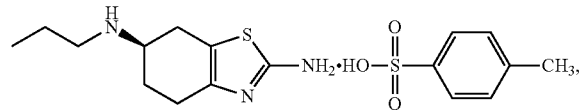

Compound $1_{(HOTs)}$ wherein the solvent is acetonitrile, a mixture of acetonitrile and water, IPA, a mixture of IPA and water, a mixture of acetonitrile and IPA, or a mixture of acetonitrile, IPA and water;
b) isolating the solid Compound $1_{(HOTs)}$ formed in step a;
c) forming a mixture comprising Compound $1_{(HOTs)}$, IPA and water, and heating the mixture to a temperature from about 70° C. to about 85° C. (for example from about 72° C. to about 83° C., from about 75° C. to about 80° C. or about 78° C.);
d) cooling the mixture to a temperature from about −5° C. to about 15° C. (for example from about 0° C. to about 10° C., from about 3° C. to about 7° C. or about 5° C.);
e) isolating the solid Compound $1_{(HOTs)}$ formed in step d;
f) forming a biphasic mixture comprising Compound $1_{(HOTs)}$, 2-methyltetrahydrofuran and brine, wherein the brine has a salt content of about 2-20% (for example about 10-14%, about 11-13% or about 12%);
g) contacting the mixture with sodium hydroxide to form Compound 1

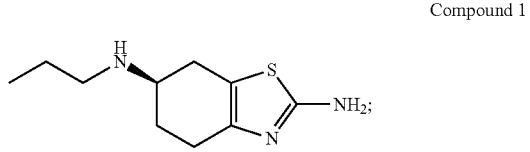

Compound 1 h) forming a mixture comprising Compound 1, 2-methyltetrahydrofuran and IPA;

i) contacting the mixture with HCl; and j) isolating the solid Compound $1_{(2HCl\cdot H2O)}$ produced in step i.

In one embodiment of this aspect, the solvent is acetonitrile. In a further embodiment, the solvent is a mixture of acetonitrile and water. In another embodiment, the solvent is IPA. In a further embodiment, the solvent is a mixture of IPA and water. In another embodiment, the solvent is a mixture of acetonitrile and IPA. In a further embodiment, the solvent is a mixture of acetonitrile, IPA and water. In some embodiments, water is present from about 0% to about 10% by weight in the mixture of acetonitrile and water. In one embodiment, the ratio of the mixture of acetonitrile to water in step a is from about 3:1 wt/wt to about 199:1 wt/wt (for example from about 7:1 to about 79:1, from about 19:1 to about 49:1 or about 39:1). In another embodiment, n-PrOTs is added to the mixture with rapid stirring. In another embodiment, the mixture comprising Compound 2, acetonitrile, water and n-PrOTs is heated to a temperature from about 60° C. to about 90° C. (for example, from about 65° C. to about 85° C. from about 68° C. to about 82° C. from about 70° C. to about 80° C.). In another embodiment, the mixture comprising Compound 2, acetonitrile, water and n-PrOTs, after being heated to a temperature from about 60° C. to about 90° C. (for example, from about 65° C. to about 85° C., from about 68° C. to about 82° C. or from about 70° C. to about 80° C.), is then stirred for about 6-16 hours (for example about 7-10 hours, about 8-10 hours, about 8-9 hours or about 9-10 hours).

In some embodiments, the solvent is a mixture of acetonitrile, IPA and water, and water is present in an amount from about 0% to about 10% (for example from about 0.5% to about 5%, from about 1.0% to about 3.0%, or about 1.4%) by weight of the mixture, acetonitrile is present in an amount from about 0% to about 50% (for example from about 10% to about 40%, from about 20% to about 30%, or about 27%) by weight of the mixture, and IPA is present in an amount from about 0% to about 50% (for example from about 10% to about 40%, from about 20% to about 30%, or about 27%) by weight of the mixture. In a further embodiment, the solvent is a mixture of acetonitrile, IPA and water, and water is present in an amount of about 1.4% by weight of the mixture, acetonitrile is present in an amount of about 27% by weight of the mixture, and IPA is present in an amount of about 27% by weight of the mixture.

In one embodiment, the solvent is a mixture of acetonitrile, IPA and water, and the resulting product Compound $1_{(HOTs)}$ is obtained at a higher yield compared to the same process using other solvent systems. In one embodiment, the yield is greater than 70%. In another embodiment, the yield is greater than 80%. In still another embodiment, the yield is greater than 83%. In a further embodiment, the yield is about 83.8%. In another embodiment, the solvent is a mixture of acetonitrile, IPA and water, and the resulting product Compound $1_{(HOTs)}$ is obtained in a more purified state compared to the same process using other solvent systems. In one embodiment, the chemical purity of the product is greater than 95%. In another embodiment, the chemical purity of the product is greater than 97%. In another embodiment, the chemical purity of the product is greater than 98%. In another embodiment, the chemical purity of the product is greater than 98.5%. In another embodiment, the chemical purity of the product is about 98.74%.

In one embodiment, the ratio of IPA to water in step c above is from about 2.3:1 v/v to about 4.25:1 v/v (for example from about 2.5:1 to about 3.3:1 or about 3:1). In another embodiment, the mixture in step d is cooled over a period from about 2 hours to about 5 hours (for example from about 2.5 hours to about 4.5 hours, from about 2.8 hours to about 4.2 hours, from about 3 hours to about 4 hours, 3.25 hours, 3.5 hours or 3.75 hours). In some embodiments, the step of isolating the solid Compound $1_{(HOTs)}$ in step e is done using filtration. In some further embodiments, the filter cake is washed once or twice with 2 volumes of IPA.

In one embodiment, the yield of Compound $1_{(HOTs)}$ isolated in step e is greater than 75%. In a further embodiment, the yield is greater than 80%. In a further embodiment, the yield is greater than 81%. In a further embodiment, the yield is greater than 82%. In a further embodiment, the yield is greater than 83%. In another further embodiment, the yield is greater than 84%. In another further embodiment, the yield is greater than 85%. In another embodiment, the yield is from about 83% to about 85%. In another embodiment, the yield is about 83.6%. In another embodiment, the yield is about 83.9%. In another embodiment, the yield is from about 84% to about 85%.

In one embodiment, the chemical purity of Compound $1_{(HOTs)}$ isolated in step e is greater than 90%. In a further embodiment, the chemical purity is greater than 95%. In a further embodiment, the chemical purity is greater than 98%. In another embodiment, the chemical purity is about 98.2%. In another embodiment, the chemical purity is about 97.1%.

In one embodiment, the enantiomeric excess of Compound $1_{(HOTs)}$ isolated in step e is from about 1% to about 15% greater than the enantiomeric excess of the starting Compound 2. In a further embodiment, the enantiomeric excess is from about 3% to about 13% greater. In a further embodiment, the enantiomeric excess is from about 4% to about 11% greater. In another embodiment, the enantiomeric excess is from about 3% to about 6% greater. In a further embodiment, the enantiomeric excess is from about 4% to about 5% greater. In a further embodiment, the enantiomeric excess is about 4.2% greater. In another embodiment, the enantiomeric excess is from about 8% to about 12% greater. In a further embodiment, the enantiomeric excess is from about 9% to about 11% greater. In a further embodiment, the enantiomeric excess is from about 10% to about 11% greater. In a further embodiment, the enantiomeric excess is about 10.1% greater. In another embodiment, the enantiomeric excess is about 1.21% greater.

In one embodiment, the ratio of 2-methyltetrahydrofuran to brine in step f is from about 3:1 v/v to about 1:1 v/v (for example, from about 2.5:1 to about 1.5:1, from about 2:1 to about 1.6:1 or about 1.8:1).

In one embodiment, the sodium hydroxide in step g is present in from about 1.0 molar equivalents to 5 molar equivalents (for example, about 1-4, about 1-3, about 1-2, about 1-1.5, about 1-1.25, about 1-1.10 or about 1.04 molar equivalents). In another embodiment, sodium hydroxide is added to the biphasic mixture with rapid stirring. In another embodiment, sodium hydroxide is added to the biphasic mixture as a 1.0 N-3.0 N solution, for example about a 2.0 N solution. In a further embodiment, the organic phase of the biphasic mixture comprising the product is used in the next step of the process without further purification of the product.

In one embodiment of this aspect, the ratio of 2-methyltetrahydrofuran to IPA in step h is from about 3:1 v/v to about 1:1 v/v (for example, from about 2.5:1 to about 1.5:1, from about 2:1 to about 1.6:1 or about 1.8:1).

In some embodiments, HCl in a solvent is added to the mixture comprising Compound 1, 2-methyltetrahydrofuran and IPA. In one further embodiment, the HCl solution is added with rapid stirring, for example 145 rpm. In another further embodiment, the HCl is added to the mixture as a solution in IPA. In still another further embodiment, the HCl solution is produced by diluting concentrated HCl with IPA to 5-10 times (for example 6-9 times, 7-8.5 times, 7.5-8.0 times, 7.7 times or 7.8 times) the original volume of concentrated HCl. In another embodiment, the HCl is present in an amount of about 2-4 (for example 2-3, 2-2.5, 2-2.2 or about 2.0) molar equivalents. In some embodiments, the final mixture is held at a temperature of about 20° C. prior to isolating the solid Compound $1_{(2HCl\text{-}H2O)}$ produced in step i. In one embodiment, the solid Compound $1_{(2HCl\text{-}H2O)}$ produced in step i is isolated by filtration. In a further embodiment, the filter cake is washed once or twice with about 2 volumes of about 3-7 wt/wt % water in IPA or about 5 wt/wt % water in IPA.

In one aspect, the process further comprises the steps of:
a) forming a mixture comprising Compound $1_{(2HCl\text{-}H2O)}$, IPA and water;
b) heating the mixture to a temperature from about 60° C. to about 90° C. (for example, from about 65° C. to about 85° C., from about 70° C. to about 82° C. or from about 75° C. to about 80° C.);
c) cooling the mixture to about 35-60° C. (for example, about 40-55° C., about 44° C. or about 50° C.);
d) removing water from the mixture;
e) cooling the solution to a temperature from about −10° C. to about 15° C. (for example, from about −5° C. to about 1° C. or from about 0° C. to about 5° C.); and
f) isolating the solid Compound $1_{(2HCl\text{-}H2O)}$.

In one embodiment, the ratio of IPA to water in step a is from about 27:1 to about 2:1 (for example, from about 14:1 to about 4:1, from about 9.3:1 to about 6:1 or about 8:1). In one embodiment, the mixture is heated in step b over a time period of about 0.5-2 hours (for example, about 0.8-1.5 hours or about 1.0 hours). In a further embodiment, the heated mixture from step b is stirred for an additional 30-60 minutes.

In one embodiment, the mixture is cooled in step c over a time period of about 0.5-2 hours (for example, about 0.8-1.5 hours or about 1.0 hours). In a further embodiment, the mixture is stirred for an additional 25-35 minutes.

In one embodiment, water is removed from the mixture in step d by azeotropic distillation of IPA and water. In a further embodiment, the distillation is performed at reduced pressure. In still a further embodiment, the distillation is performed at a pressure from about 90 Torr to about 170 Torr (for example, from about 100 Torr to about 150 Torr, from about 110 Torr to about 130 Torr or from about 120 Torr to about 125 Torr). In another further embodiment, the pressure during distillation is ramped from about 140 Torr to about 160 Torr in the beginning of the distillation to from about 90 Torr to about 110 Torr at the end of the distillation (for example, about 150 Torr at the beginning of the distillation to about 100 Torr at the end of the distillation). In another further embodiment, IPA is added to the mixture during distillation. In some embodiments, the water content of the solution after performing step d is about 0-20% (for example, about 1-16%, about 2-14%, about 3-12%, about 4-10%, about 5-8%, about 5.5-6.5% or about 6%).

In a another embodiment, step d of the process further includes the steps of:

a) reducing the volume of the mixture by distillation at reduced pressure;
b) diluting the mixture with IPA; and
c) optionally repeating steps a and b one or more times.

In one further embodiment, the water content of the resulting mixture is about 3-10%.

In one embodiment, the process further comprises the step of adding a specific volume of IPA to the mixture to produce a final water content in the supernatant portion of the mixture of about 6%, wherein the specific volume of IPA is determined by performing the calculation: Final volume (mL) of IPA to be added to the mixture=((24×KF×S)/(1−6.5×KF))−(2.4×KF), wherein "KF" is the water content, expressed as a decimal, as determined by the Karl Fischer method, and "S" is the weight in grams of starting compound of formula $I_{(2HCl\text{-}H2O)}$.

In one embodiment, the yield of Compound $1_{(2HCl\text{-}H2O)}$ produced by crystallization from a solution containing Compound $1_{(2HCl\text{-}H2O)}$, IPA and water is greater than 80%. In a further embodiment, the yield is greater than 90%. In a further embodiment, the yield is greater than 93%. In another further embodiment, the yield is greater than 94%. In one embodiment, the yield is 94-96%.

In one embodiment, the chemical purity of Compound $1_{(2HCl\text{-}H2O)}$ produced by crystallization from a solution containing Compound $1_{(2HCl\text{-}H2O)}$, IPA and water is greater than 90%. In a further embodiment, the chemical purity is greater than 95%.

In a further embodiment, the chemical purity is greater than 98%. In a further embodiment, the chemical purity is greater than 99%. In a further embodiment, the chemical purity is greater than 99.5%. In a further embodiment, the chemical purity is greater than 99.8%. In a further embodiment, the chemical purity is greater than 99.9%.

In one embodiment, the enantiomeric excess of Compound $1_{(2HCl\text{-}H2O)}$ produced by crystallization from a solution containing Compound $1_{(2HCl\text{-}H2O)}$, IPA and water is greater than about 80%. In further embodiment, the enantiomeric excess is greater than 85%. In further embodiment, the enantiomeric excess is greater than 97%. In further embodiment, the enantiomeric excess is greater than 98%. In further embodiment, the enantiomeric excess is greater than 99%. In further embodiment, the enantiomeric excess is greater than 99.5%. In further embodiment, the enantiomeric excess is greater than 99.9%. In further embodiment, the enantiomeric excess is greater than 99.95%. In further embodiment, the enantiomeric excess is greater than 99.99%. In one embodiment, the enantiomeric excess of Compound $1_{(2HCl\text{-}H2O)}$ produced by crystallization from a solution containing Compound $1_{(2HCl\text{-}H2O)}$, IPA and water is from about 98% to about 100%. In one embodiment, the enantiomeric excess of Compound $1_{(2HCl\text{-}H2O)}$ produced by crystallization from a solution containing Compound $1_{(2HCl\text{-}H2O)}$, IPA and water is from about 99% to about 100%. In one embodiment, the enantiomeric excess of Compound $1_{(2HCl\text{-}H2O)}$ produced by crystallization from a solution containing Compound $1_{(2HCl\text{-}H2O)}$, IPA and water is about 100%.

In one aspect, the solid Compound $1_{(2HCl\text{-}H2O)}$ isolated from the process is in the polymorphic Form A. In one embodiment, Compound $1_{(2HCl\text{-}H2O)}$ Form A is a hydrate. In a further embodiment, Compound $1_{(2HCl\text{-}H2O)}$ Form A is a monohydrate.

Figure 2:
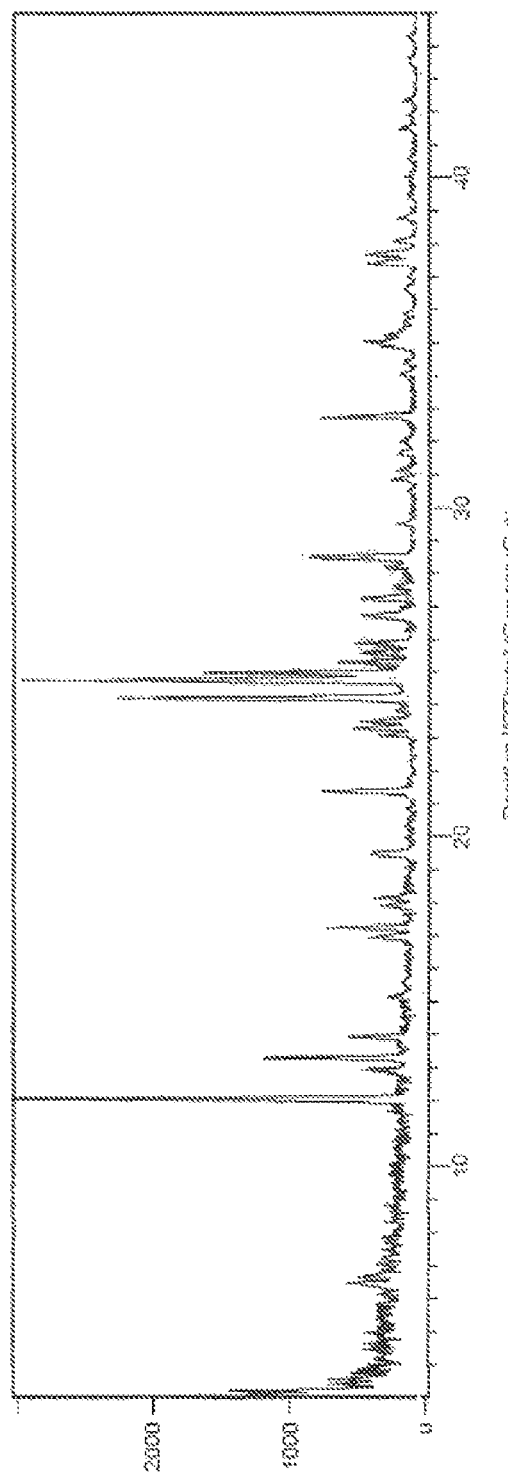
FIG. 2 is an XRPD pattern of Compound $1_{(2HCl-H2O)}$, Form A.

In one embodiment, Compound $1_{(2HCl\text{-}H2O)}$ Form A is produced by a process described herein. In a further embodiment, the Compound $1_{(2HCl\text{-}H2O)}$ Form A produced by a process described herein has a water content of from about 3% to about 10% (for example, from about 4% to about 8%, from about 5% to about 7%, or about 6%). In a further embodiment, Compound $1_{(2HCl\text{-}H2O)}$ Form A is produced by crystallization from a solution containing Compound $1_{(2HCl\text{-}H2O)}$, IPA and water. In a further embodiment, the solution contains greater than 5% water, relative to IPA. In another further embodiment, the solution contains greater than 6% water, relative to IPA. In still another further embodiment, the solution contains greater than 7% water, relative to IPA. In one embodiment, the XRPD pattern produced from a sample of Compound $1_{(2HCl\text{-}H2O)}$ Form A is similar to that shown in FIG. 2. In a further embodiment, the sample of Compound 1 dihydrochloride Form A which produced an XRPD pattern similar to that shown in FIG. 2 is produced by a method described herein.

Figure 3:
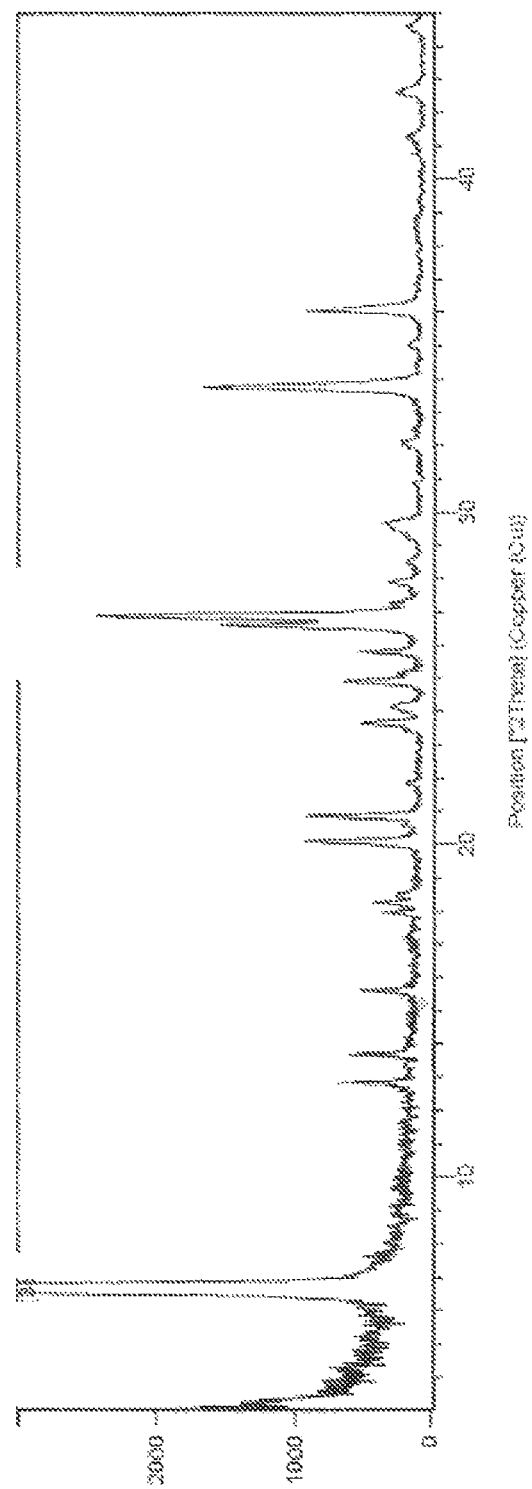
FIG. 3 is an XRPD pattern of Compound 1 dihydrochloride, Form B.

In one aspect, the solid Compound 1 dihydrochloride isolated from the process is in the polymorphic Form B. In one embodiment, Compound 1 dihydrochloride Form B is an anhydrate. In a further embodiment, Compound 1 dihydrochloride Form B is produced by crystallization from a solution containing Compound $1_{(2HCl\text{-}H2O)}$, IPA and water. In another further embodiment, the solution contains less than 3% water, relative to IPA. In still another further embodiment, the solution contains less than 2% water, relative to IPA. In still another further embodiment, the solution contains less than 0.5% water, relative to IPA. In another embodiment, Compound $1_{(2HCl\text{-}H2O)}$ Form B is produced by crystallization from a solution containing Compound 1 dihydrochloride and anhydrous IPA. In one embodiment, the XRPD pattern produced from a sample of Compound 1 dihydrochloride Form B is similar to that shown in FIG. 3. In a further embodiment, the sample of Compound 1 dihydrochloride Form B which produced an XRPD pattern similar to that shown in FIG. 3 is produced by a method described herein.

In one embodiment, Compound 1 dihydrochloride Form B is produced by removing water from a sample of Compound $1_{(2HCl\text{-}H2O)}$ Form A. In a further embodiment, water is removed from a solid sample of Compound $1_{(2HCl\text{-}H2O)}$ Form A by a drying process. In a further embodiment, the solid sample of Compound $1_{(2HCl\text{-}H2O)}$ Form A is dried in an oven, optionally at elevated temperatures.

In one embodiment, Compound 1 dihydrochloride Form B is produced by removing water from a sample of Compound $1_{(2HCl\text{-}H2O)}$ Form A by contacting said Form A with an anhydrous solvent, such as anhydrous IPA. In further embodiment, a mixture of Compound 1 dihydrochloride Form B and Compound $1_{(2HCl\text{-}H2O)}$ Form A is produced by contacting a sample of said Form A produced by a process described herein with an anhydrous solvent, such as anhydrous IPA. In still a further embodiment, the Compound $1_{(2HCl\text{-}H2O)}$ Form A filter cake, produced by a process described herein is rinsed with anhydrous IPA to produce a mixture of Compound 1 dihydrochloride Form B and Compound $1_{(2HCl\text{-}H2O)}$ Form A. In another further embodiment, the weight percent of Compound 1 dihydrochloride Form B in the mixture is dependent on the amount of time that a sample of Compound $1_{(2HCl\text{-}H2O)}$ Form A is in contact with an anhydrous solvent such as anhydrous IPA. In some embodiments, a mixture of Compound 1 dihydrochloride Form B and Compound $1_{(2HCl\text{-}H2O)}$ Form A is produced by contacting a sample of Compound $1_{(2HCl\text{-}H2O)}$ Form A with an anhydrous solvent, such as anhydrous IPA for longer than 1 hour (for example, longer than 1.5 hours, longer than 2 hours, about 2.25 hours or about 5 hours). In other embodiments, contacting Compound $1_{(2HCl\text{-}H2O)}$ Form A with an anhydrous solvent, such as anhydrous IPA, for 1 hour or less does not produce any detectable Compound 1 dihydrochloride Form B.

It is understood that the production of Compound 1 dihydrochloride Form B from Compound $1_{(2HCl\text{-}H2O)}$ Form A by contacting said Form A with a solvent is a function of 1) the amount of water in the solvent, and 2) the amount of time said Form A is in contact with said solvent. The above factors relating to the solvent will, to a large degree, dictate the ratio of Compound 1 dihydrochloride Form B to Compound $1_{(2HCl\text{-}H2O)}$ Form A in the resulting sample.

Formulations, Administrations and Uses

The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

General Synthetic Strategies

A general synthetic strategy to produce compounds of formula II is shown in Scheme 1.

Scheme 1

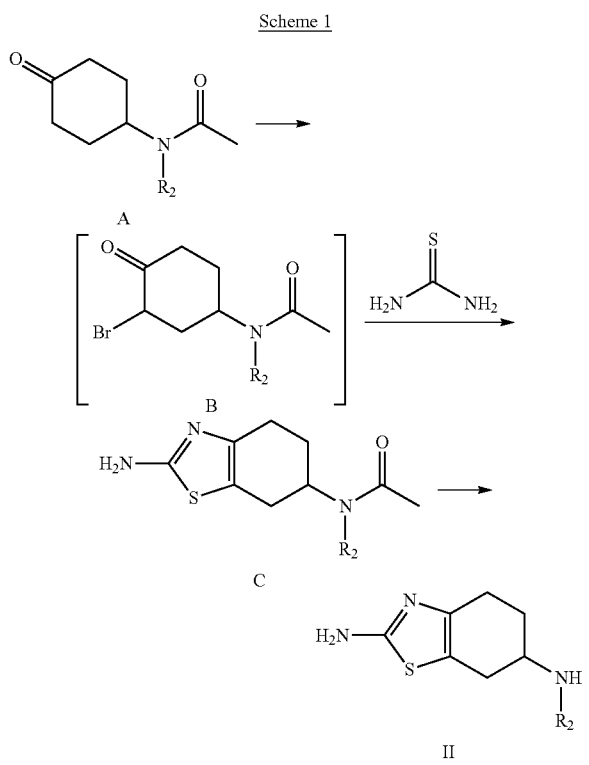

A compound of formula A can be brominated using a reagent such as molecular bromine or N-bromosuccinimide to produce an intermediate of formula B. Intermediate B can then be contacted with thiourea to provide a tetrahydrobenzothiazole intermediate of formula C. The intermediate C can be synthesized from A with or without isolation of intermediate B. Hydrolysis of C to a racemic intermediate of formula II can be performed using basic conditions such as aqueous NaOH or $Na_2CO_3$, or by acidic conditions such as HCl, $H_2SO_4$ or HBr. The intermediate of formula II can be synthesized from A with or without isolation of intermediate B or C. The steps leading to the formation of a racemic intermediate of formula II can be performed in separate reaction vessels or one reaction vessel, with or without isolation of one or more of intermediates A, B or C. A racemic intermediate of formula II can be enantiomerically enriched by selective crystallization of the acid addition salt of a single enantiomer using a chiral acid such as tartaric acid.

A general scheme to produce compounds of formula $I_{(2HCl \cdot H2O)}$ is shown in Scheme 2.

Scheme 2

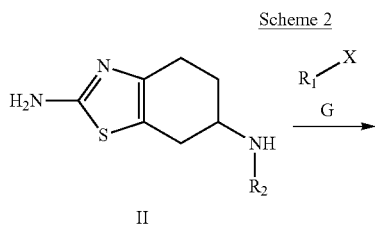

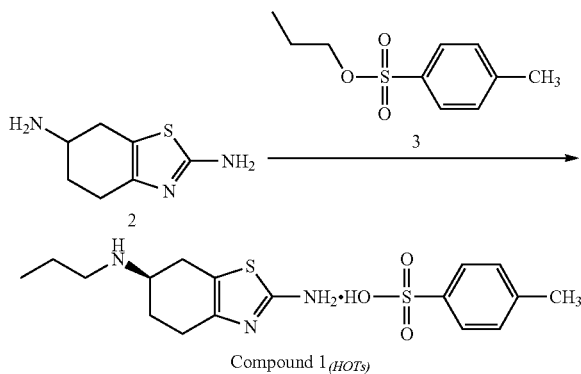

A compound of formula II can be treated with an alkylating reagent of formula G, wherein $R_1$ is an alkyl group and X is a leaving group, according to Scheme 2. The mono-salt intermediate F, wherein HX is a bound acid such as HCl, HBr, MsOH or TsOH, can be directly converted to the dihydrochloride salt by ion exchange. Alternatively, F can first be converted to the free base and then converted to the dihydrochloride salt by the addition of HCl.

EXAMPLES

Example 1: (R)-(+)-2-amino-4,5,6,7-tetrahydro-6-(n-propylamino)benzothiazole p-toluenesulfonic acid salt ($1_{(HOTs)}$)

Method 1:

Compound 2 (100 g, 590.9 mmol, 98.8% ee) was charged in a 1 L reactor equipped with nitrogen inlet, condenser, thermometer and overhead stirrer at room temperature. Acetonitrile (487.5 mL, 4.875 Volumes) was added to the reactor and agitation was started. Water (12.5 mL, 0.125 Volumes) was then added to the reactor, followed by DIPEA (38.2 g, 295 mmol). n-Propyl p-toluenesulfonate (189.9 g, 886 mmol) was then added to the reactor and the reaction mixture was heated to about 75 to 80° C. with stirring. The reaction stirred at about 75 to 80° C. for 6-16 hours, until complete (typically about 8-10 hours). The batch was then cooled to room temperature over 2-3 hours and aged at room temperature for additional 1 hour. The reaction mixture was filtered at room temperature, and the wet cake was washed with acetonitrile (250 mL) twice and dried to a constant weight to provide the product in 83.9% yield (190.1 g), 98.2% purity (determined by achiral HPLC), and about 100% ee.

Method 2:

Compound 2 (100 g, 591.0 mmol, 98.8% ee) was charged in a reactor equipped with nitrogen inlet, condenser, thermometer and overhead stirrer at room temperature. Water (10.0 g) was added to the reactor, followed by acetonitrile (390.0 g), and rapid agitation was started. DIPEA (38.2 g, 295 mmol) was then added to the reactor, followed by n-Propyl p-toluenesulfonate (189.9 g, 886 mmol) and the resulting mixture was heated to about 75 to 80° C. with stirring. The reaction stirred at about 75 to 80° C. for 6-16 hours, until complete (typically about 8-10 hours). The batch was then cooled to about 20° C. over about 3 hours and stirred at about 20° C. for additional 1 hour. The reaction mixture was filtered at room temperature, and the wet cake was washed with acetonitrile (300 mL) twice, and dried to a constant weight to provide the product in 84-85% yield, 98.2% purity (determined by achiral HPLC), and about 100% ee.

Method 3:

Compound 2 (1500 g, 8.86 mol, 98.8% ee) was charged in a reactor equipped with nitrogen inlet, condenser, thermometer and overhead stirrer at room temperature. Acetonitrile (5752 g) was added to the reactor, followed by water (188 g), and agitation at 70 rpm was started. DIPEA (572.7 g, 4.43 mol) was then added to the reactor, followed by n-Propyl p-toluenesulfonate (2848.7 g, 13.29 mol) and the resulting mixture was heated to about 75 to 80° C. with stirring (jacket temperature was 82° C.). The reaction stirred at about 75 to 80° C. for about 8.5-9 hours. The batch was then cooled to about 15° C. over about 3 hours and stirred at about 15° C. overnight. The reaction mixture was filtered at room temperature, and the wet cake was washed with acetonitrile (3 L) twice and dried to a constant weight to provide the product in 83.6% yield, 97.1% purity (determined by achiral HPLC), and about 100% ee.

Method 4:

In an appropriately sized reaction vessel, Compound 2 (10.00 g, 59.08 mmol), Compound 3 (18.99 g, 88.63 mmol), N,N-Diisopropylethylamine (3.818 g, 29.54 mmol), Acetonitrile (25.0 mL, 479 mmol) and Isopropyl alcohol (25.0 mL, 326 mmol) were mixed and heated at 75° C. for 16 hours. The resulting reaction mixture was then cooled to about 20° C., filtered, and the wet cake was washed with Acetonitrile. The product was air dried under vacuum to provide 19.34 g (85.34%) Compound $1_{(HOTs)}$, having a chemical purity of 98.65%.

Method 5:

In an appropriately sized reaction vessel, Compound 2 (10.00 g, 59.08 mmol), Compound 3 (18.99 g, 88.63 mmol), N,N-Diisopropylethylamine (3.818 g, 29.54 mmol), water (1.00 mL; 55.5 mmol), Acetonitrile (25.0 mL, 479 mmol) and Isopropyl alcohol (25.0 mL, 326 mmol) were mixed and heated at 78° C. for 10 hours, and then cooled at 20° C. overnight. The resulting reaction mixture was then filtered, and the wet cake was washed with Acetonitrile (30 mL×2). The product was air dried under vacuum to provide 18.99 g (83.80%) Compound $1_{(HOTs)}$, having a chemical purity of 98.74%. Method 6:

In an appropriately sized reaction vessel, Compound 2 (50.00 g, 295.4 mmol), Compound 3 (94.96 g, 443.1 mmol), N,N-Diisopropylethylamine (38.18 g, 295.4 mmol) and Isopropyl alcohol (350.0 mL, 4572 mmol) were mixed and heated from 25° C. to 80° C. over 60 minutes, and then stirred at 80° C. for 14 hours. The reaction was then cooled to 20° C. over 1 hour and aged at 20° C. for an additional 1 hour. The resulting reaction mixture was then filtered, and the wet cake was washed with Isopropyl alcohol (100 mL×2). The product was air dried under vacuum overnight to provide 91.72 g (78.12%) Compound $1_{(HOTs)}$, at 96.5% chemical purity.

Example 2: Recrystallization and purification of (R)-(+)-2-amino-4,5,6,7-tetrahydro-6-(n-propylamino)benzothiazole p-toluenesulfonic acid salt ($1_{(HOTs)}$)

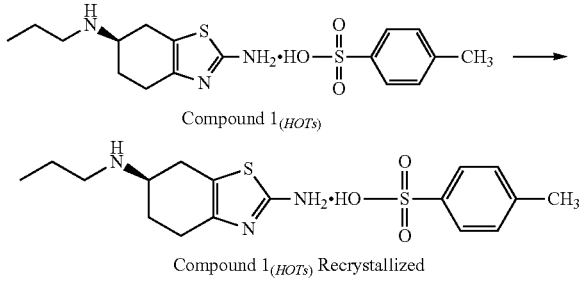

Compound $1_{(HOTs)}$

Compound $1_{(HOTs)}$ Recrystallized

Compound $1_{(HOTs)}$ (2.7 kg, 7.039 mol) was charged to a reactor at room temperature followed by 2-Propanol (IPA, 16.97 kg, 8 Volumes) and the mixture was stirred at 100 rpm. Water (7.29 kg, 2.7 Volumes) was then added to the reaction mixture and the mixture was heated to about 78° C. until a clear solution was observed. The batch was cooled to about 5° C. over a period of about 4 hours and stirred at 135 rpm for an additional 1 hour. The batch was then filtered and washed two times with IPA (5.4 L, 2 Volumes). The filter cake was dried at 60° C. under vacuum to provide the product in 90% yield, greater than 99.5% purity by HPLC and about 100% ee.

Example 3: Synthesis of (R)-(+)-2-amino-4,5,6,7-tetrahydro-6-(n-propylamino)benzothiazole (1)

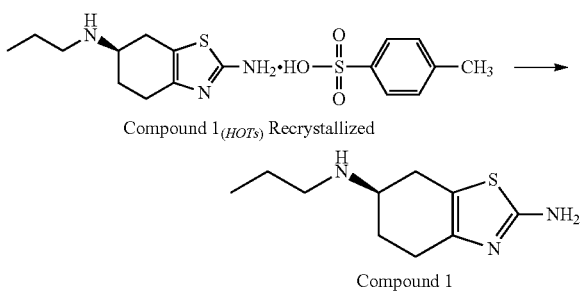

Compound $1_{(HOTs)}$ Recrystallized

Compound 1

Method 1:

Recrystallized Compound $1_{(HOTs)}$ (1.20 Kg, 3.13 mol) was charged to a reactor, followed by 2-MeTHF (9.6 Kg, 10.8 L, 9 Volumes) and 12% brine solution (6.57 Kg, 6.0 L, 5 Volumes). The biphasic reaction mixture was then stirred at 125 rpm. A 2.0 N NaOH solution (1.61 L, 1.04 equivalent) was added to the stirred solution and stirring continued until all solids had dissolved (about 20 minutes). Stirring was then stopped to allow the layers to separate, and the aqueous layer was drained and extracted once with 2-MeTHF (3.2 Kg, 3.6 L, 3 Volumes). The combined organic extracts were then washed twice with water (1.2 L, 1 Volume). The organic layer was washed once with IPA (6.0 L, 5.0 Volumes).

Method 2:

Recrystallized Compound 1$_{(HOTs)}$ (1.20 Kg, 3.13 mol) was charged to a reactor, followed by 2-MeTHF (9.6 Kg, 10.8 L, 9 Volumes) and 12% brine solution (6.57 Kg, 6.0 L, 5 Volumes). The biphasic reaction mixture was then stirred at 125 rpm. A 2.0 N NaOH solution (1.61 L, 1.04 equivalent) was added to the stirred solution and stirring continued until all solids had dissolved (about 20 minutes). Stirring was then stopped to allow the layers to separate, and the aqueous layer was drained and extracted once with 2-MeTHF (3.2 Kg, 3.6 L, 3 Volumes). The combined organic extracts were then washed with water (2×1.2 L, 2×1 Volume).

Example 4: Synthesis of (R)-(+)-2-amino-4,5,6,7-tetrahydro-6-(n-propylamino)benzothiazole dihydrochloride (1$_{(2HCl-H2O)}$)

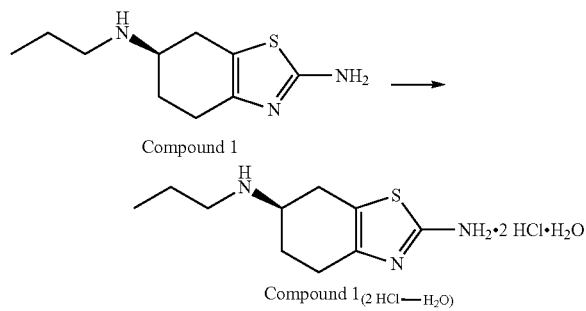

The organic solution from Example 3 was charged with IPA (4.75 Kg, 6.0 L, 5 Volumes) and the mixture was stirred. Concentrated HCl (2 eq.) was diluted with IPA (3.6 L, 3.0 Volumes), and the resulting acid mixture was added to the first mixture containing Compound 1 over about 1 hour with good agitation. During the addition, the mixture was kept at a temperature between 20-30° C. A precipitate formed and the mixture was cooled to about 20° C. and held for about 30 minutes. The mixture was then filtered and the filter cake was washed once with 2 volumes of a 19:1 wt/wt mixture of IPA to water solution, and then dried at 45-50° C. under vacuum to give 89% molar yield. The HPLC purity (at 265 nm) of this dried material was about 100%, with about 100% ee.

Example 5: Recrystallization and purification of (R)-(+)-2-amino-4,5,6,7-tetrahydro-6-(n-propylamino)benzothiazole dihydrochloride (1$_{(2HCl-H2O)}$)

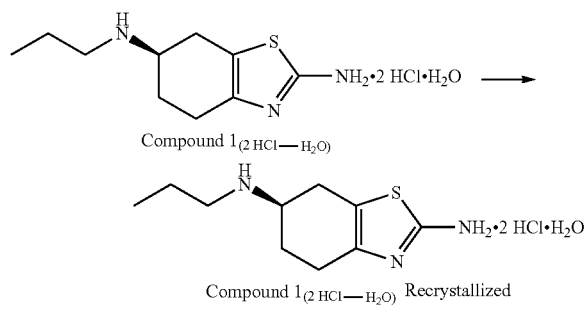

Method 1:

Compound 1$_{(2HCl-H2O)}$ (700 g) was added to a reaction vessel, followed by IPA (4354 mL) and water (546 mL). The mixture was stirred and heated to a temperature of about 70-75° C. over 1 hour, and then stirred for an additional 30-60 minutes. The solution was then cooled over about 1 hour to about 50° C. and the slurry was stirred for 30-60 minutes. The mixture was then connected to a vacuum and distilled while gradually reducing the pressure to about 150 Torr until the volume of the mixture was reduced by about 50%. IPA (2000 mL) was added to the mixture and the vacuum step was repeated as above. IPA (2000 mL) was added and the mixture was cooled over 1-1.5 hour to a temperature of about 0-5° C., stirred for 30-60 minutes and the solid Compound 1$_{(2HCl-H2O)}$ product was filtered. The filter cake was washed in two portions with a cold solution containing about 1330 mL IPA and about 70 mL water. The filter cake was then dried to provide the product in 97% yield, about 100% purity by HPLC and about 100% ee.

Method 2:

Compound 1$_{(2HCl-H2O)}$ (70 g, 1 equivalent) was added to a reaction vessel, followed by IPA (341.5 g, 435 mL, 6.22 Volumes) and water (54.6 mL, 0.78 Volumes). The mixture was stirred and heated to a temperature of about 75-80° C. and then stirred for an additional 30 minutes. The mixture was then cooled over about 1 hour to about 50° C. and stirred for about 30 minutes. The mixture was then connected to a vacuum and distilled at a pressure of about 150 Torr at the start to about 100 Torr at the end until the volume of the mixture was reduced to about 3 volumes. IPA (164.9 g, 210 mL, 3 Volumes) was added at 45-55° C. over a period of about 10 minutes to the mixture. The amount of final charge of IPA that leads to a 6% final water content was determined using the equation: Final charge of IPA=((24×KF×S)/(1−6.5×KF))−(2.4×KF). In this equation, "KF" is the water content as determined by the Karl Fischer method (for example, if 7.5% water content is measured, 0.075 is the KF value in the equation), and "S" is the weight in grams of starting compound of Compound 1$_{(2HCl-H2O)}$. The amount of IPA determined from the equation above was then added to the mixture at 45-55° C. over 8 minutes. The mixture was then cooled to a temperature of about 0° C. over 2 hours, and stirred at 0° C. for an additional 1-2 hours. The solid Compound 1$_{(2HCl-H2O)}$ product was then filtered and the filter cake was washed with 1 volume of a mixture containing 5% water in IPA. The filter cake was then dried at a pressure of 30 Torr for 12-16 hours to provide the product as polymorph A in 94-96% yield, with about 100% ee and having a water content of about 6.0±0.2%.

The product Compound 1$_{(2HCl-H2O)}$ was characterized by $^1$H NMR, producing a spectrum consistent with that shown in FIG. 1.

Example 6: Determination of Compound 1$_{(2HCl-H2O)}$ Polymorphic Form A

As determined by Solvent/Polymorph screening, Compound 1$_{(2HCl-H2O)}$ Form A is a monohydrate bis-HCl salt and Compound 1$_{(2HCl-H2O)}$ Form B is an anhydrate bis-HCl salt. Form A is a thermodynamic hydrate form while Form B is a stable anhydrate form. Form B converts to Form A under exposure to humidity and/or moisture.

Two crystallization experiments were carried out using two different rates. One experiment with a fast cooling, 0.75° C./min from 80° C. to 5° C. in 100 minutes, and the other with a slow cooling, 0.15° C./min from 80° C. to 5° C.

in 480 minutes. Solids precipitated throughout these cooling periods were analyzed by x-ray diffraction (XRPD) to verify the polymorphic form.

The crystal Form B, the anhydrate form of Compound $1_{(2HCl-H2O)}$, is formed when Form A is in contact with dry IPA. Tables 1A and 1B below summarize the results of experiments showing the conversion of the Compound $1_{(2HCl-H2O)}$ filter cake from Form A to Form B upon contact with dry IPA during cake washing.

TABLES 1A and 1B

Comparison of cake wash using aqueous and non-aqueous (dry) IPA

Table 1A: First Cake Wash

| Wash Composition (v/v) | Wet Cake Initial Weight | Wash I Vol | Soak Time | XRPD |
|---|---|---|---|---|
| 5% H2O/IPA | 46 g | 100 ml | 1 h | Form A |
| 7.5% H2O/IPA | 42 g | 100 ml | 2.25 h | Form A |
| non-aqueous IPA | 46 g | 100 ml | 1 h | Form A |
| non-aqueous IPA | 42 g | 100 ml | 2.25 h | mix Form A, B |

Table 1B: Second Cake Wash

| Wash Composition (v/v) | Wet Cake Initial Weight | Wash II Vol | Soak Time | XRPD |
|---|---|---|---|---|
| 5% H2O/IPA | 46 g | 100 ml | 1 h | Form A |
| 7.5% H2O/IPA | 42 g | 100 ml | 5 h | Form A |
| non-aqueous IPA | 46 g | 100 ml | 1 h | mix Form A, B |
| non-aqueous IPA | 42 g | 100 ml | 5 h | mix Form A, B |

Example 7: Increased Yield of Compound $1_{(2HCl-H2O)}$ Polymorphic Form a by Azeotropic Distillation at Reduced Pressure Form A is highly soluble in water and is formed in a solvent system containing water. Recrystallization of Compound $1_{(2HCl-H2O)}$ Form A is performed in a binary IPA/H2O system where IPA is an anti-solvent. A previous recrystallization process yielded about 80% product, and was carried out in ca. 6.7 volumes of an 8:1 v/v mixture of IPA to water. The amount and solvent composition were chosen as to prevent product precipitation during the clarifying filtration step (80-85° C.) prior to cooling to 0-5° C. A procedure was developed to increase the yield (>90%) and possibly reduce particle agglomeration. The modified procedure involves removal of water by distillation after initially crystallizing the product from the same 8:1 v/v IPA/Water composition (~14% w/w).

Since the product is highly soluble in water, yield improvement can be achieved by reducing the amount of water from the initial composition (13.8% w/w). This can be accomplished after first crystallizing the product (to desired Form A) followed by distillation to remove water from the mixture.

Thermodynamics of a Binary IPA-Water System

IPA (2-Propanol) forms an azeotropic composition with water. The mixture of 88% IPA and 12% water boils at 80° C. under atmospheric conditions (1.01325 Bar) and the distillate (vapor phase) will have the same composition as the boiling liquid phase. The phase diagram for a binary IPA/water system shows that water can be removed by distillation under azeotropic conditions at atmospheric pressures starting from about 82% IPA (18% water) and temperature ranges of 80-82° C.

The ranges of azeotropic conditions for a IPA-Water binary system under different pressures, from atmospheric to reduced pressure (vacuum), is tabulated in Table 2. This azeotropic composition was predicted at selected system pressures using UNIFAC group contribution with Dyno-Chem software (DynoChem; 2011 Version 4.0.0.0; Performance Fluid Dynamics Ltd.).

TABLE 2

Predicted 'Azeotropic' Composition in Binary 2-Propanol-Water System Under Various Total Pressures

| Composition (water content w/w) | Pressure | Temperature (boiling point) |
|---|---|---|
| 10-18% | 1000 mbar (760 Torr) | 79-82° C. |
| 9-15% | 657 mbar (500 Torr) | 70-72° C. |
| 8-15% | 263 mbar (200 Torr) | 50-52° C. |
| 7-15% | 197 mbar (150 Torr) | 44-46° C. |
| 6-16% | 131 mbar (100 Torr) | 36-38° C. |
| 9-16% | 53 mbar (40 Torr) | 21-23° C. |

Distillation Procedure for Adjustment of Water Contents

Azeotropic distillation for removal of water is performed under reduced pressure to lower the boiling point of the IPA/water azeotrope to maintain a slurry of Compound $1_{(2-HCl-H2O)}$ during the distillation and minimize loss of bound water (hydrate).

At temperatures below 50° C. some product crystals (monohydrate, Form A) precipitate out of solution (13.8% water in IPA). As the volume of the mixture is reduced during distillation, the remaining product crystals (monohydrate, Form A) also form.

The crystallization characteristics of Compound $1_{(2HCl-H2O)}$ in an 8:1 (v/v) IPA to Water solvent system show that in 7 volumes of a 14% water in IPA solvent system, Compound $1_{(2HCl-H2O)}$ can be expected to completely dissolve at temperatures greater than 75° C., and nucleate upon cooling at temperatures between 50-60° C.

Compound $1_{(2HCl-H2O)}$ was initially dissolved in 7 volumes of a 13.8 wt % water in IPA at 80° C. and cooled to 50° C. to produce some crystals. The pressure was then reduced to about 150 Torr (~200 mBar) and the mixture distilled at 40-45° C. Distillation was discontinued when the volume of the mixture in the reactor decreased by about half. At this point, the water content in the mixture remained about 13.8 wt % and more product precipitated out. A prescribed amount of IPA was then added to the reactor to increase the volume, resulting in a total water content of about 6-7 wt % in the mixture. This procedure is repeated once to obtain the final water content 3-5 wt %. Table 3 summarized the results using this procedure.

TABLE 3

Compound $1_{(2HCl-H2O)}$ Recrystallization with Distillation

| | Run 1 | Run 2 | Run 3 |
|---|---|---|---|
| Compound $1_{(2HCl-H2O)}$ Crude input | 700 g | 700 g | 3700 g |
| Yield | 96.7% | 98.0% | 96% |
| XRPD | Conforms to Crystal Form A | Conforms to Crystal Form A | Conforms to Crystal Form A |

TABLE 3-continued

Compound $1_{(2HCl\text{-}H2O)}$ Recrystallization with Distillation

| | Run 1 | Run 2 | Run 3 |
|---|---|---|---|
| DSC | Conforms to Crystal Form A | Conforms to Crystal Form A | — |
| Water Content dry API (w/w), KF | 5.83% | 5.76% | 6.1% |
| Final Water Content in Pot (w/w), KF | 3.9% | 4% | 3.9% |
| HPLC AP | >99.9% RRT 0.67: 0.01% RRT 1.18: 0.006% RRT 1.30: 0.006% | >99.9% RRT 0.42: 0.016% RRT 0.67: 0.014% RRT 1.30: 0.008% | >99.9% |
| HPLC Chiral | 100% R | 100% R | >99.9% R |
| 2-Propanol content (wt %), NMR> | 0.26% | 0.33% | 0.20% |
| Chloride (23.46% Theory) | 22.09%* | 22.09%* | — |

Table 3 shows that the product met the specification for chemical and chiral purity and was confirmed as Form A. Some examples resulted in water content below theoretical level for monohydrate (5.95% wt) with no indication of a presence of anhydrous crystal Form B. This material was re-slurried in a solution of 5 wt % water in IPA for 24 hours in order to bring up the water level.

An improved recrystallization procedure (Example 5, Method 2) was developed to improve operational aspects of the distillation process. In this improved procedure, the final water level in the pot is controlled to be within 5-7% wt.

Control of Compound $1_{(2HCl\text{-}H2O)}$ Form A by Reduced Pressure Distillation The conversion of Form A (hydrate) to Form B (anhydrate) is mediated by exposure of Form A to non-aqueous 2-Propanol or thermally by heating the solid to around 120°.

In this process, only crystal Form A precipitates upon cooling a solution of Compound $1_{(2HCl\text{-}H2O)}$ in ~13% aqueous 2-propanol. These crystals of Form A remain in contact with aq. 2-propanol (7-13% water) throughout the distillation and are filtered out of a 5-7% aqueous solution after the final water content adjustment by adding 2-propanol.

In an anomalous case where mixed crystals a forms A & B are produced, they can be reconverted to Form A completely by re-slurrying in an aqueous 2-propanol solution.

Example 8: Improved Enantiomeric Purity of the Tosylate Salt of Pramipexole by Precipitation from an ACN:Water Solution (Spiking Study)

Enantiomerically pure (R)-2,6-diamino-4,5,6,7-tetrahydrobenzothiazole was prepared through a classical resolution process from the racemate. Therefore, (R)-2,6-diamino-4,5,6,7-tetrahydrobenzothiazole was expected to contain some of its enantiomeric isomer (S)-2,6-diamino-4,5,6,7-tetrahydrobenzothiazole as an impurity. To understand the fate of this impurity, a spiking study was employed. In this study, (S)-2,6-diamino-4,5,6,7-tetrahydrobenzothiazole was used as the starting material to produce pramipexole p-toluenesulfonic acid salt, the enantiomeric isomer of Compound $1_{(HOTs)}$, under selected alkylation reaction conditions. The data are summarized in Table 5. The conclusion from this study was that (S)-2,6-diamino-4,5,6,7-tetrahydrobenzothiazole with an enantiomeric excess of 89% could be converted to pramipexole p-toluenesulfonic acid salt with an enantiomeric excess of 98% and (S)-2,6-diamino-4,5,6,7-tetrahydrobenzothiazole with an enantiomeric excess of 95% could be converted to pramipexole p-toluenesulfonic acid salt with an enantiomeric excess of 99% by the process disclosed herein. Since Compound $1_{(HOTs)}$ and pramipexole p-toluenesulfonic acid salt are enantiomeric isomers, the results should apply to Compound $1_{(HOTs)}$ as well. Therefore, (R)-2,6-diamino-4,5,6,7-tetrahydrobenzothiazole with an enantiomeric excess of 89% could be converted to Compound $1_{(HOTs)}$ with an enantiomeric excess of 98% and (R)-2,6-diamino-4,5,6,7-tetrahydrobenzothiazole with an enantiomeric excess of 95% could be converted to Compound $1_{(HOTs)}$ with an enantiomeric excess of 99% by the process disclosed herein.

TABLE 5

Enantiomeric purity spiking study

| Solvent (X = volumes) | Rxn temp | Rxn time | (S)-diamine ee % | Comp $1_{(HOTs)}$ % | Pram-OTs % | Pram-OTs ee % |
|---|---|---|---|---|---|---|
| ACN 5 X | 80 C. | 16 h | 94.58 | 0.89 | 99.11 | 98.22 |
| ACN 5 X | 80 C. | 16 h | 88.69 | 2.06 | 97.94 | 95.88 |
| 2.5% H2O/ACN 5 X | 75 C. | 8 h | 94.58 | 1.01 | 98.99 | 97.98 |
| 2.5% H2O/ACN 5 X | 75 C. | 8 h | 89.22 | 2.33 | 97.67 | 95.34 |

Example 9: Karl Fischer Titration (USP <921> Method 1a) [General Description]

Principle

The titrimetric determination of water is based upon the quantitative reaction of water with an anhydrous solution of sulfur dioxide and iodine in the presence of a buffer that reacts with hydrogen ions.

In the original titrimetric solution, known as Karl Fischer Reagent, the sulfur dioxide and iodine are dissolved in pyridine and methanol. The test specimen may be titrated with the Reagent directly, or the analysis may be carried out by a residual titration procedure. The stoichiometry of the reaction is not exact, and the reproducibility of a determination depends upon such factors as the relative concentrations of the Reagent ingredients, the nature of the inert solvent used to dissolve the test specimen, and the technique used in the particular determination.

Therefore, an empirically standardized technique is used in order to achieve the desired accuracy. Precision in the method is governed largely by the extent to which atmospheric moisture is excluded from the system. The titration of water is usually carried out with the use of anhydrous methanol as the solvent for the test specimen; however, other suitable solvents may be used for special or unusual test specimens.

Apparatus

Any apparatus may be used that provides for adequate exclusion of atmospheric moisture and determination of the endpoint. In the case of a colorless solution that is titrated directly, the endpoint may be observed visually as a change in color from canary yellow to amber. The reverse is observed in the case of a test specimen that is titrated residually. More commonly, however, the endpoint is determined electrometrically with an apparatus employing a simple electrical circuit that serves to impress about 200 mV of applied potential between a pair of platinum electrodes immersed in the solution to be titrated. At the endpoint of the titration a slight excess of the reagent increases the flow of current to between 50 and 150 microamperes for 30 seconds to 30 minutes, depending upon the solution being titrated. The time is shortest for substances that dissolve in the reagent. With some automatic titrators, the abrupt change in current or potential at the endpoint serves to close a solenoid-operated valve that controls the buret delivering the titrant. Commercially available apparatus generally comprises a closed system consisting of one or two automatic burets and a tightly covered titration vessel fitted with the necessary electrodes and a magnetic stirrer. The air in the system is kept dry with a suitable desiccant, and the titration vessel may be purged by means of a stream of dry nitrogen or current of dry air.

Reagent

Prepare the Karl Fischer Reagent as follows. Add 125 g of iodine to a solution containing 670 mL of methanol and 170 mL of pyridine, and cool. Place 100 mL of pyridine in a 250-mL graduated cylinder, and, keeping the pyridine cold in an ice bath, pass in dry sulfur dioxide until the volume reaches 200 mL. Slowly add this solution, with shaking, to the cooled iodine mixture. Shake to dissolve the iodine, transfer the solution to the apparatus, and allow the solution to stand overnight before standardizing. One mL of this solution when freshly prepared is equivalent to approximately 5 mg of water, but it deteriorates gradually; therefore, standardize it within 1 hour before use, or daily if in continuous use. Protect from light while in use. Store any bulk stock of the reagent in a suitably sealed, glass-stoppered container, fully protected from light, and under refrigeration.

A commercially available, stabilized solution of Karl Fischer type reagent may be used. Commercially available reagents containing solvents or bases other than pyridine or alcohols other than methanol may be used also. These may be single solutions or reagents formed in situ by combining the components of the reagents present in two discrete solutions. The diluted Reagent called for in some monographs should be diluted as directed by the manufacturer. Either methanol or other suitable solvent, such as ethylene glycol monomethyl ether, may be used as the diluent.

Test Preparation

Unless otherwise specified in the individual monograph, use an accurately weighed or measured amount of the specimen under test estimated to contain 2 to 250 mg of water. The amount of water depends on the water equivalency factor of the Reagent and on the method of endpoint determination.

In most cases, the minimum amount of specimen, in mg, can be estimated using the formula:

$$FCV/KF$$

in which F is the water equivalency factor of the Reagent, in mg per mL; C is the used volume, in percent, of the capacity of the buret; V is the buret volume, in mL; and KF is the limit or reasonable expected water content in the sample, in percent. C is between 30% and 100% for manual titration, and between 10% and 100% for the instrumental method endpoint determination.

Where the specimen under test is an aerosol with propellant, store it in a freezer for not less than 2 hours, open the container, and test 10.0 mL of the well-mixed specimen. In titrating the specimen, determine the endpoint at a temperature of 10 or higher.

Where the specimen under test is capsules, use a portion of the mixed contents of not fewer than 4 capsules.

Where the specimen under test is tablets, use powder from not fewer than 4 tablets ground to a fine powder in an atmosphere of temperature and relative humidity known not to influence the results.

Where the monograph specifies that the specimen under test is hygroscopic, use a dry syringe to inject an appropriate volume of methanol, or other suitable solvent, accurately measured, into a tared container, and shake to dissolve the specimen. Using the same syringe, remove the solution from the container and transfer it to a titration vessel prepared as directed for Procedure. Repeat the procedure with a second portion of methanol, or other suitable solvent, accurately measured, add this washing to the titration vessel, and immediately titrate. Determine the water content, in mg, of a portion of solvent of the same total volume as that used to dissolve the specimen and to wash the container and syringe, as directed for Standardization of Water Solution for Residual Titrations, and subtract this value from the water content, in mg, obtained in the titration of the specimen under test. Dry the container and its closure at 100 for 3 hours, allow to cool in a desiccator, and weigh. Determine the weight of specimen tested from the difference in weight from the initial weight of the container.

Standardization of the Reagent

Place enough methanol or other suitable solvent in the titration vessel to cover the electrodes, and add sufficient Reagent to give the characteristic endpoint color, or 100±50 microamperes of direct current at about 200 mV of applied potential.

For determination of trace amounts of water (less than 1%), it is preferable to use Reagent with a water equivalency factor of not more than 2.0.

Sodium tartrate may be used as a convenient water reference substance. Quickly add 75 to 125 mg of sodium tartrate ($C_4H_4Na_2O_6\text{-}2H_2O$), accurately weighed by difference, and titrate to the endpoint. The water equivalence factor F, in mg of water per mL of reagent, is given by the formula:

$$2(18.02/230.08)(W/V)$$

in which 18.02 and 230.08 are the molecular weights of water and sodium tartrate dihydrate, respectively; W is the weight, in mg, of sodium tartrate dihydrate; and V is the volume, in mL, of the Reagent consumed in the second titration.

For the precise determination of significant amounts of water (1% or more), use Purified Water as the reference substance. Quickly add between 25 and 250 mg of water, accurately weighed by difference, from a weighing pipet or from a precalibrated syringe or micropipet, the amount taken being governed by the reagent strength and the buret size, as referred to under Volumetric Apparatus 31. Titrate to the endpoint. Calculate the water equivalence factor, F, in mg of water per mL of reagent, by the formula:

$$W/V$$

in which W is the weight, in mg, of the water; and V is the volume, in mL, of the reagent required.

Procedure

Unless otherwise specified, transfer 35 to 40 mL of methanol or other suitable solvent to the titration vessel, and titrate with the Reagent to the electrometric or visual endpoint to consume any moisture that may be present. (Disregard the volume consumed, since it does not enter into the calculations.) Quickly add the Test Preparation, mix, and again titrate with the Reagent to the electrometric or visual endpoint. Calculate the water content of the specimen, in mg, taken by the formula:

SF in which S is the volume, in mL, of the Reagent consumed in the second titration; and F is the water equivalence factor of the Reagent.

Example 10: X-Ray Powder Diffraction Spectroscopy (XRPD) Characterization of the Polymorphic Forms of Compound $1_{(2HCl\text{-}H2O)}$ XRPD studies were performed using a (CubiX-Pro XRD). Samples were placed on Si zero-return ultra-micro sample holders. Analysis was performed using a 10 mm irradiated width, and the following parameters were set within the hardware/software:
X-ray tube: Cu KV, 45 kV, 40 mA
Detector: X'Celerator
ASS Primary Slit: Fixed 1°
Divergence Slit (Prog): Automatic—5 mm irradiated length
Soller Slits: 0.02 radian
Scatter Slit (PASS): Automatic—5 mm observed length
Scan Range: 3.0-45.0°
Scan Mode: Continuous
Step Size: 0.03°
Time per Step: 10 s
Active Length: 2.54°

Following analysis, the data was converted from adjustable to fixed slits using the X'Pert HighScore Plus software with the following parameters:
Fixed Divergence Slit Size: 1.00°, 1.59 mm
Crossover Point: 44.3° Omega The XRPD pattern of Compound $1_{(2HCl\text{-}H2O)}$ Form A is shown in FIG. 2. The XRPD pattern of Compound 1 dihydrochloride Form B is shown in FIG. 3.

Other Embodiments

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims.

What is claimed is:

1. A process for preparing a compound of formula $I_{(HOTs)}$ formula $I_{(HOTs)}$

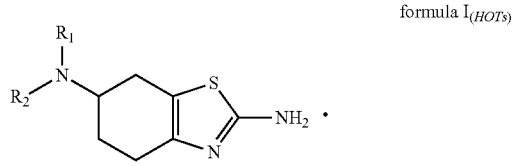

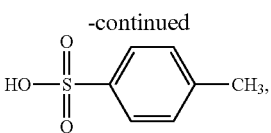

wherein $R_1$ and $R_2$ are each independently hydrogen or $C_{1-6}$ alkyl, wherein each $C_{1-6}$ alkyl is optionally and independently substituted with up to 3 occurrences of $C_{1-6}$ alkyl, aryl or heteroaryl;

the process comprising contacting a mixture, which comprises a compound of formula II formula II

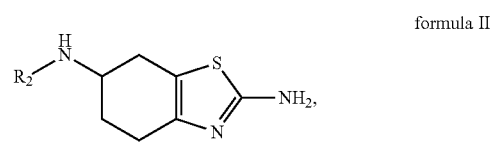

and a solvent, with a compound having the formula

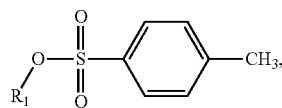

in the presence of a base, to provide a compound of formula $I_{(HOTs)}$, wherein the solvent is acetonitrile, a mixture of acetonitrile and water, IPA, a mixture of IPA and water, a mixture of acetonitrile and IPA, or a mixture of acetonitrile, IPA and water; isolating the compound of formula $I_{(HOTs)}$,
 a) forming a mixture comprising the compound of formula $I_{(HOTs)}$, IPA and water, and heating the mixture to about 70° C. to about 85° C.;
 b) cooling the mixture to about 5° C. to about 15° C.; and
 c) isolating the solid compound of formula $I_{(HOTs)}$ formed during step b).

2. The process of claim 1, wherein $R_2$ is hydrogen.

3. The process of claim 1, wherein $R_1$ is $C_{1-6}$ alkyl.

4. The process of claim 3, wherein $R_1$ is n-propyl.

5. The process of claim 1, wherein the solvent is a mixture of acetonitrile and water, a mixture of IPA and water, a mixture of acetonitrile and IPA, or a mixture of acetonitrile, IPA and water.

6. The process of claim 5, wherein the solvent is a mixture of acetonitrile and water.

7. The process of claim 6, wherein water present is about 0% to about 10% by weight in the mixture of acetonitrile and water.

8. The process of claim 7, wherein the ratio of the mixture of acetonitrile to water is about 37:1 wt/wt.

9. The process of claim 5, wherein the solvent is a mixture of acetonitrile, IPA and water.

10. The process of claim 9, wherein the water present is about 0% to about 10% by weight of the mixture, the acetonitrile present is about 0% to about 50% by weight of the mixture, and the IPA present is about 0% to about 50% by weight of the mixture.

11. The process of claim 1, wherein the stereochemistry of the carbon atom to which the —$NR_1(R_2)$ moiety is attached is in the (R) configuration.

12. The process of claim 1, wherein the base is triethylamine, DIPEA, pyridine or DBU.

13. The process of claim 12, wherein the base is DIPEA.

14. The process of claim 1, wherein the ratio of IPA to water in step a) is about 2.3:1 v/v to about 4.25:1 v/v.

15. The process of claim 1, wherein the ratio of IPA to water in step a) is about 2:1 v/v.

16. The process of claim 1, further comprising the process of producing a compound of formula I

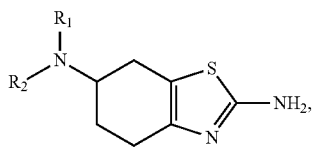

formula I the process comprising the steps of:
d) forming a biphasic mixture comprising a compound of formula $I_{(HOTs)}$, 2-methyltetrahydrofuran and brine, wherein the brine has a salt content of about 2-20% by weight; and
e) contacting the mixture with a base to produce a compound of formula I.

17. The process of claim 16, wherein the ratio of 2-methyltetrahydrofuran to brine in step d) is about 3.1:1 v/v to about 1:1 v/v.

18. The process of claim 16, wherein the ratio of 2-methyltetrahydrofuran to brine in step d) is about 1.8:1 v/v.

19. The process of claim 16, wherein the base is sodium hydroxide, potassium hydroxide, sodium carbonate or potassium carbonate.

20. The process of claim 19, wherein the base is sodium hydroxide.

21. The process of claim 20, wherein the sodium hydroxide is present in about 1 molar equivalent.

22. The process of claim 16, further comprising preparing a compound of formula $I_{(2\ HCl-H2O)}$

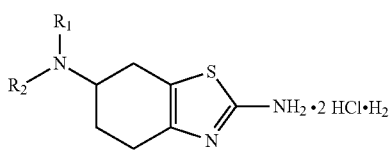

formula $I_{(2HCl-H2O)}$ comprising the steps of:
f) forming a mixture comprising a compound of formula I, 2-methyltetrahydrofuran and IPA;
g) contacting the mixture with HCl; and
h) isolating the solid compound of formula $I_{(2\ HCl-H2O)}$ produced in step g).

23. The process of claim 22, wherein the ratio of 2-methyltetrahydrofuran to IPA in step f) is about 3.1:1 v/v to about 1.1 v/v.

24. The process of claim 23, wherein the ratio of 2-methyltetrahydrofuran to IPA in step f) is about 1.8:1 v/v.

25. The process of claim 22, wherein HCl in a solvent is added to the mixture comprising a compound of formula I, 2-methyltetrahydrofuran and IPA.

26. The process of claim 25, wherein the HCl is added to the mixture as a solution in IPA.

27. The process of claim 22, wherein the HCl is present in an amount of about 2 molar equivalents.

28. The process of claim 22, further comprising the steps of:)
i) forming a mixture comprising compound $1_{(2Hcl-H2O)}$, IPA and water;
j) heating the mixture to a temperature of about 60° C. to about 90° C.;
k) cooling the mixture to about 35° C. to about 60° C.;
l) removing water from the mixture;
m) cooling the solution to a temperature of about −10° C. to about 15° C.; and
n) isolating the solid Compound $1_{(2HCl-H2O)}$.

29. The process of claim 28, wherein the ratio of IPA to water in step i) is about 27:1 to about 6:1.

30. The process of claim 28, wherein the ratio of IPA to water in step i) is about 6:1.

31. The process of claim 28, wherein water is removed from the solution in step l) by azeotropic distillation of IPA and water.

32. The process of claim 31, wherein the distillation is performed at reduced pressure.

33. The process of claim 28, wherein step 41 of the process further includes the steps of:
i. reducing the volume of the mixture by distillation at reduced pressure;
ii. diluting the mixture with IPA; and
iii. optionally repeating steps i. and ii. one or more times.

34. The process of claim 33, wherein the water content of the resulting mixture is about 3-10%.

35. The process of claim 33, further comprising the step of adding a specific volume of IPA to the mixture to produce a final water content in the supernatant portion of the mixture of about 6%, wherein the specific volume of IPA is determined by performing the calculation: Final volume (mL) of IPA to be added to the mixture=((24×KF×S)/(1−6.5×KF))−(2.4×KF), wherein "KF" is the water content, expressed as a decimal, as determined by the Karl Fischer method, and "S" is the weight in grams of starting compound of formula $I_{(2HCl-H2O)}$.

36. A process for preparing Compound $1_{(2\ HCl-H2O)}$

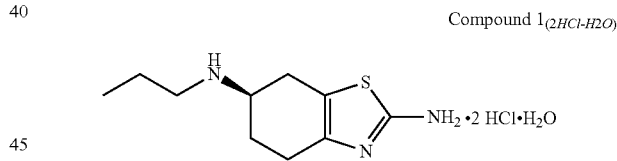

Compound $1_{(2HCl-H2O)}$ wherein the process comprises the steps of:
a) contacting a mixture comprising Compound 2

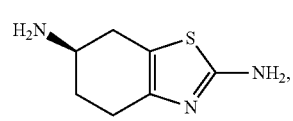

Compound 2 and a solvent, with n-PrOTs and DIPEA to provide Compound $1_{(HOTs)}$

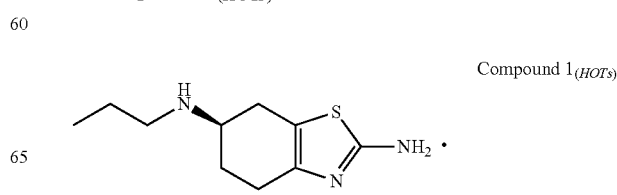

Compound $1_{(HOTs)}$

-continued

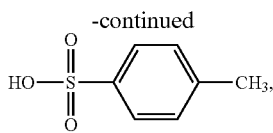

wherein the solvent is acetonitrile, a mixture of acetonitrile and water, IPA, a mixture of IPA and water, a mixture of acetonitrile and IPA, or a mixture of acetonitrile, IPA and water;
b) isolating the solid Compound $1_{(HOTs)}$ formed in step a);
c) forming a mixture comprising Compound $1_{(HOTs)}$, IPA and water, and heating the mixture to a temperature of about 60° C. to about 90° C.;
d) cooling the mixture to a temperature of about −5° C. to about 15° C.;
e) isolating the solid Compound $1_{(HOTs)}$ formed in step d);
f) forming a biphasic mixture comprising Compound $1_{(HOTs)}$, 2-methyltetrahydrofuran and brine, wherein the brine has a salt content of about 2-20% by weight;
g) contacting the mixture with sodium hydroxide to form Compound 1

Compound 1 h) forming a mixture comprising Compound 1, 2-methyltetrahydrofuran and IPA;
i) contacting the mixture with HCl; and
j) isolating the solid Compound $1_{(2\ HCl\text{-}H2O)}$ produced in step i).

37. The process of claim 36, wherein the temperature in step c) is about 70° C. to about 80° C.
38. The process of claim 37, wherein the temperature in step c) is about 75° C. to about 80° C.
39. The process of claim 36, wherein the temperature in step d) is about 0° C. to about 10° C.
40. The process of claim 36, wherein the solvent is a mixture of acetonitrile and water, a mixture of IPA and water, a mixture of acetonitrile and IPA, or a mixture of acetonitrile, IPA and water.
41. The process of claim 34, wherein the solvent is a mixture of acetonitrile and water.
42. The process of claim 41, wherein the water present is about 0% to about 10% by weight in the mixture of acetonitrile and water.
43. The process of claim 42, wherein the ratio of acetonitrile to water in step a) is about 37:1 wt/wt.
44. The process of claim 36, wherein the ratio of IPA to water in step c) is about 2.3:1 to about 4.25:1 v/v.
45. The process of claim 44, wherein the ratio of IPA to water in step c) is about 2.5:1.
46. The process of claim 36, wherein the brine in step f) has a salt content of about 12%.
47. The process of claim 36, wherein the ratio of 2-methyltetrahydrofuran to brine in step f) is about 3:1 to about 1:1 v/v.
48. The process of claim 47, wherein the ratio of 2-methyltetrahydrofuran to brine in step f) is about 1:1 v/v.
49. The process of claim 36, wherein the ratio of 2-methyltetrahydrofuran to IPA in step h) is about 1.8:1 v/v.
50. The process of claim 36, further comprising the steps of:
k) forming a mixture comprising Compound $1_{(2\ HCl\text{-}H2O)}$, IPA and water;
l) heating the mixture to a temperature of about 60° C. to about 90° C.;
m) cooling the solution to a temperature of about 35° C. to about 60° C.;
n) removing water from the solution;
o) cooling the solution to a temperature of about −10° C. to about 15° C.; and
p) removing the solid Compound $1_{(2HCl\text{-}H2O)}$ from the liquid phase.
51. The process of claim 50, wherein the temperature in step l) is about 75° C. to about 80° C.
52. The process of claim 50, wherein the temperature in step m) is about 40° C.
53. The process of claim 50, wherein the temperature in step m) is about 50° C.
54. The process of claim 50, wherein the ratio of IPA to water in step k) is about 8:1.
55. The process of claim 50, wherein water is removed from the solution in step n) by azeotropic distillation of IPA and water.
56. The process of claim 55, wherein the distillation is performed at reduced pressure.
57. The process of claim 50, wherein step n) of the process further includes the steps of:
i. reducing the volume of the mixture by distillation at reduced pressure;
ii. diluting the mixture with IPA; and
iii. optionally repeating steps i. and ii. one or more times.
58. The process of claim 57, wherein the water content of the resulting mixture is about 3-12%.
59. The process of claim 58, wherein the water content of the resulting mixture is about 5.5% to about 6.5%.
60. The process of claim 59, wherein the water content of the resulting mixture is about 6%.
61. The process of claim 57, further comprising the step of adding a specific volume of IPA to the mixture to produce a final water content in the supernatant portion of the mixture of about 6%, wherein the specific volume of IPA is determined by performing the calculation: Final volume (mL) of IPA to be added to the mixture=((24×KF×S)/(1−6.5×KF))−(2.4×KF), wherein "KF" is the water content, expressed as a decimal, as determined by the Karl Fischer method, and "S" is the weight in grams of starting compound of Compound $1_{(2\ HCl\text{-}H2O)}$.
62. The process of claim 57, wherein the solid Compound $1_{(2\ HCl\text{-}H2O)}$ isolated from the process is in the polymorphic Form A.
63. The process of claim 62, wherein the water content of the solid Compound $1_{(2HCl\text{-}H2O)}$ in the polymorphic Form A is about 5% to about 7% as determined by the Karl Fischer method.
64. A process for preparing Compound $1_{(2HCl\text{-}H2O)}$ Compound $1_{(2HCl\text{-}H2O)}$

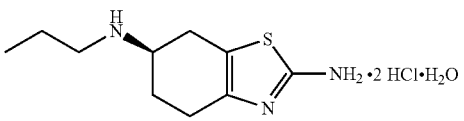

wherein the process comprises the steps of:

a) contacting a mixture comprising Compound 2

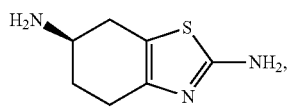
Compound 2 and a solvent, with n-PrOTs and DIPEA to provide Compound $1_{(HOTs)}$

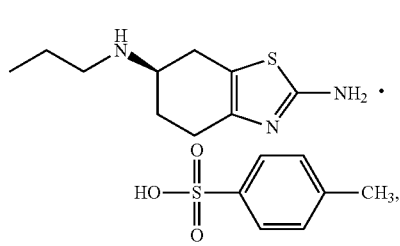
Compound $1_{(HOTs)}$ wherein the solvent is a mixture of acetonitrile and water;

b) isolating the solid Compound $1_{(HOTs)}$ formed in step a);
c) forming a mixture comprising Compound $1_{(HOTs)}$, IPA and water, and heating the mixture to a temperature of about 75° C., wherein the ratio of IPA to water is about 2.5:1;
d) cooling the mixture to a temperature from about 0° C. to about 10° C.;
e) isolating the solid Compound $1_{(HOTs)}$ formed in step d);
f) forming a biphasic mixture comprising Compound $1_{(HOTs)}$, 2-methyltetrahydrofuran and brine, wherein the brine has a salt content of about 12% by weight and wherein the ratio of 2-methyltetrahydrofuran to brine is about 1:1;
g) contacting the mixture with sodium hydroxide to form Compound 1

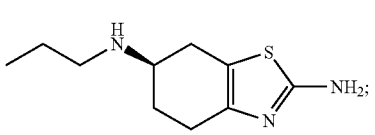
Compound 1 h) forming a mixture comprising Compound 1, 2-methyltetrahydrofuran and IPA;
i) contacting the mixture with HCl; and
j) isolating the solid Compound $1_{(2HCl\text{-}H2O)}$ produced in step i).

65. The process of claim 64, further comprising the steps of:

k) forming a mixture comprising Compound $1_{(2HCl\text{-}H2O)}$, IPA and water, wherein the ratio of IPA to water is 8:1;
l) heating the mixture to a temperature of about 75° C. to about 80° C.;
m) cooling the solution to a temperature of about 40° C. to about 55° C.;
n) removing water from the solution;
o) cooling the solution to a temperature of about −10° C. to about 15° C.; and
p) removing the solid Compound $1_{(2HCl\text{-}H2O)}$ from the liquid phase.

* * * * *